(12) United States Patent
Rudman

(10) Patent No.: US 9,888,984 B2
(45) Date of Patent: Feb. 13, 2018

(54) SELF-LIGATING ORTHODONTIC BRACKET WITH ROTATABLE CLOSURE MEMBER

(71) Applicant: Ormco Corporation, Orange, CA (US)

(72) Inventor: Robert T. Rudman, Denver, CO (US)

(73) Assignee: Ormco Corporation, Orange, CA (US)

( * ) Notice: Subject to any disclaimer, the term of this patent is extended or adjusted under 35 U.S.C. 154(b) by 190 days.

(21) Appl. No.: 14/305,684

(22) Filed: Jun. 16, 2014

(65) Prior Publication Data

US 2014/0370454 A1 Dec. 18, 2014

Related U.S. Application Data

(60) Provisional application No. 61/835,329, filed on Jun. 14, 2013.

(51) Int. Cl.
*A61C 3/00* (2006.01)
*A61C 7/28* (2006.01)

(52) U.S. Cl.
CPC .................... *A61C 7/285* (2013.01)

(58) Field of Classification Search
CPC ..... A61C 8/0022; A61C 8/005; A61C 8/0089; A61C 8/006; A61C 8/0069
USPC .......................................................... 433/10
See application file for complete search history.

(56) References Cited

U.S. PATENT DOCUMENTS

| 2,011,575 A | 8/1935 | Ford |
| 2,104,192 A | 1/1938 | Ford |
| 3,084,437 A | 4/1963 | Neger |
| 3,158,934 A | 12/1964 | Waldman |
| 3,238,619 A | 3/1966 | Brunson et al. |
| 3,469,315 A | 9/1969 | Russ |
| 3,633,277 A | 1/1972 | Reichel |

(Continued)

FOREIGN PATENT DOCUMENTS

| CN | 201085695 Y | 7/2008 |
| JP | 2003180712 A | 7/2003 |
| WO | 2008130613 A1 | 10/2008 |

OTHER PUBLICATIONS

The International Bureau of WIPO, International Preliminary Report on Patentability issued in International Application No. PCT/US2014/042520 dated Dec. 23, 2015.

(Continued)

*Primary Examiner* — Cris L Rodriguez
*Assistant Examiner* — Matthew Saunders
(74) *Attorney, Agent, or Firm* — Wood Herron & Evans LLP

(57) ABSTRACT

An orthodontic bracket for coupling an archwire with a tooth includes a bracket body configured to be mounted to the tooth and having an archwire slot adapted to receive the archwire therein. A rotatable closure member is movable relative to the bracket body between an opened position in which the archwire is insertable into the archwire slot, and at least one closed position in which the closure member retains the archwire in the archwire slot. The orthodontic bracket further includes a retention mechanism having a first element associated with the bracket body and a second element associated with the closure member, the first and second elements cooperating to rotatably secure the closure member to the bracket body and to provide at least one positive stop in the rotation of the closure member relative to the bracket body.

32 Claims, 27 Drawing Sheets

(56) References Cited

U.S. PATENT DOCUMENTS

| | | |
|---|---|---|
| 3,793,730 A | 2/1974 | Begg et al. |
| 4,077,126 A | 3/1978 | Pletcher |
| 4,085,506 A * | 4/1978 | Lew .................... A61C 8/0048 |
| | | 433/172 |
| 4,167,813 A | 9/1979 | Forster |
| 4,171,568 A | 10/1979 | Forster |
| 4,198,753 A | 4/1980 | Forster |
| 4,597,739 A | 7/1986 | Rosenberg |
| 4,664,626 A | 5/1987 | Kesling |
| 4,698,017 A | 10/1987 | Hanson |
| 4,712,999 A | 12/1987 | Rosenberg |
| 4,859,179 A | 8/1989 | Kesling |
| 4,867,678 A | 9/1989 | Parker |
| 4,917,602 A | 4/1990 | Broussard |
| 5,607,301 A | 3/1997 | Roman |
| 5,685,711 A | 11/1997 | Hanson |
| 5,823,771 A | 10/1998 | Nord |
| 5,857,850 A | 1/1999 | Voudouris |
| 6,071,118 A | 6/2000 | Damon |
| 6,071,119 A | 6/2000 | Christoff et al. |
| 6,241,434 B1 * | 6/2001 | Ajimi .................... B23B 31/005 |
| | | 279/75 |
| 6,247,923 B1 | 6/2001 | Vashi |
| 6,368,105 B1 | 4/2002 | Voudouris et al. |
| 6,506,049 B2 | 1/2003 | Hanson |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,659,766 B2 | 12/2003 | Abels et al. |
| 6,659,767 B2 | 12/2003 | Abels et al. |
| 6,682,345 B2 | 1/2004 | Kesling et al. |
| 6,695,612 B2 | 2/2004 | Abels et al. |
| 6,733,286 B2 | 5/2004 | Abels et al. |
| 6,776,613 B2 | 8/2004 | Orikasa |
| 6,843,651 B2 | 1/2005 | Orikasa |
| 6,866,505 B2 | 3/2005 | Senini |
| 6,932,597 B2 | 8/2005 | Abels et al. |
| 6,942,483 B2 | 9/2005 | Heiser |
| 6,960,081 B2 | 11/2005 | Abels et al. |
| 6,960,808 B2 | 11/2005 | Wang |
| 7,063,531 B2 | 6/2006 | Maijer et al. |
| 7,094,052 B2 | 8/2006 | Abels et al. |
| 7,186,114 B2 | 3/2007 | Navarro et al. |
| 7,210,927 B2 | 5/2007 | Abels et al. |
| 7,214,057 B2 | 5/2007 | Voudouris |
| 7,234,935 B2 | 6/2007 | Abels et al. |
| 7,247,018 B2 | 7/2007 | Freeman, Jr. et al. |
| 7,255,557 B2 | 8/2007 | Forster |
| 7,306,458 B1 | 12/2007 | Lu |
| 7,335,020 B2 | 2/2008 | Castner et al. |
| 7,442,039 B2 | 10/2008 | Opin et al. |
| 7,585,171 B2 | 9/2009 | Hagelganz et al. |
| 7,621,743 B2 | 11/2009 | Bathen et al. |
| 7,695,277 B1 | 4/2010 | Stevens |
| 7,717,706 B2 | 5/2010 | Forster |
| 7,959,437 B2 | 6/2011 | Zakhem et al. |
| 8,033,824 B2 | 10/2011 | Oda |
| 8,162,660 B2 | 4/2012 | Rudman |
| 8,668,411 B2 * | 3/2014 | Guy ..................... B23B 27/007 |
| | | 279/71 |
| 2002/0119414 A1 | 8/2002 | Orikasa |
| 2002/0132206 A1 | 9/2002 | Voudouris |
| 2007/0224569 A1 * | 9/2007 | Oda ........................ A61C 7/02 |
| | | 433/10 |
| 2007/0259301 A1 | 11/2007 | Hagelganz et al. |
| 2007/0259304 A1 | 11/2007 | Hagelganz et al. |
| 2007/0281269 A1 | 12/2007 | Forster |
| 2009/0130621 A1 | 5/2009 | Chikami |
| 2010/0159411 A1 * | 6/2010 | Oda ........................ A61C 7/02 |
| | | 433/11 |
| 2010/0285420 A1 * | 11/2010 | Oda ........................ A61C 7/30 |
| | | 433/11 |
| 2011/0081622 A1 | 4/2011 | Mashouf |
| 2011/0123942 A1 | 5/2011 | Rudman |
| 2011/0287378 A1 | 11/2011 | Dupray et al. |
| 2012/0288816 A1 * | 11/2012 | Dupray ................. A61C 7/143 |
| | | 433/10 |

OTHER PUBLICATIONS

European Patent Office, Supplementary European Search Report in EP10831890.8 dated Nov. 24, 2014.

International Searching Authority, International Search Report and Written Opinion in International Application No. PCT/US2014/042520, dated Sep. 25, 2014.

Japanese Patent Office, Office Action in Japanese Patent Application No. 2012-539863, dated Feb. 20, 2014.

European Patent Office, Third Party Observation in European Patent Application No. 10831890.8, dated Sep. 24, 2014.

European Patent Office, Official Action issued in related Application No. EP10831890.8 dated Nov. 17, 2016, 5 pp.

Chinese Patent Office, Office Action in Chinese Patent Application No. 201480039119.8, Nov. 16, 2017.

* cited by examiner

SELF-LIGATING ORTHODONTIC BRACKET WITH ROTATABLE CLOSURE MEMBER

CROSS REFERENCE TO RELATED APPLICATION

This application claims the benefit of U.S. Provisional Application No. 61/835,329 filed on Jun. 14, 2013, the disclosure of which is incorporated by reference herein in its entirety.

TECHNICAL FIELD

The invention relates generally to orthodontic brackets and, more particularly, to self-ligating orthodontic brackets having rotatable closure members with improved retention mechanisms.

BACKGROUND

Orthodontic brackets represent a principal component of corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or closure member, such as a latch, clip or slide, for retaining the archwire within the bracket slot.

One such closure member for retaining the archwire within the bracket slot is a rotatable clip. The rotatable clip is movably mounted to the bracket body so as to be rotatable about a central clip axis. Rotation of the clip about the central axis moves the closure member between an opened position and one or more closed positions. By way of example, the rotatable clip may have an opened position in which the clip does not block or otherwise impede the insertion of the archwire into the archwire slot of the bracket. From this position, the clip may be rotated about the central axis to a closed position wherein a portion of the clip closes off the archwire slot, thereby retaining the archwire therein. Such an orthodontic bracket is disclosed in U.S. Pat. No. 8,162,660, the disclosure of which is incorporated by reference herein in its entirety.

One challenge with self-ligating orthodontic brackets, and certainly with rotating clip orthodontic brackets, is designing an effective retention mechanism for movably coupling the clip to the bracket body. For example, in one approach, the rotating clip has a radially-extending rib that is received within an annular groove in the bracket body. Once the rib is positioned in the annular groove, such as during the assembly process, the clip may not be separated from the bracket body (such as by pulling it away from the bracket body in, for example, a buccal or labial direction), but is rotatable relative to the bracket body between its opened position and a closed position.

In addition, orthodontists and other orthodontic professionals may find it desirable to have a positive indication of when the rotating clip is in the opened position and/or a closed position. This not only notifies the orthodontist when the clip is in the opened or closed position, but also aids in preventing or reducing the possibility of accidental or unintentional movement. While the rib/groove arrangement of prior rotating clip orthodontic brackets allows the clip to rotate between its various positions, there is nothing inherent in that arrangement that provides a positive indication of clip position. If such a feature is desired, it is typically incorporated separately. By way of example, in one approach, the rotating clip includes a bump or projection which is received in a dimple or recess of the bracket body when the rotating clip is in a closed position.

While self-ligating brackets have been generally successful, manufacturers of such brackets continually strive to improve the use and functionality of these orthodontic brackets. In this regard, there exists a need for a self-ligating orthodontic bracket having a rotating clip type of closure member that has an improved retention mechanism that not only retains the clip to the bracket body, but also provides a positive indication of clip position.

SUMMARY

To these ends, an orthodontic bracket for coupling an archwire with a tooth includes a bracket body configured to be mounted to the tooth and having an archwire slot adapted to receive the archwire therein. A rotatable closure member is movable relative to the bracket body between an opened position in which the archwire is insertable into the archwire slot, and at least one closed position in which the closure member retains the archwire in the archwire slot. The orthodontic bracket further includes a retention mechanism having a first element associated with the bracket body and a second element associated with the closure member, the first and second elements cooperating to rotatably secure the closure member to the bracket body and to provide at least one positive stop in the rotation of the closure member relative to the bracket body.

In one embodiment, the closure member is rotatable between an opened position and at least two closed positions. In one of the closed positions, the closure member may be configured to provide active ligation of the archwire in the archwire slot. In another closed position, the closure member may be configured to provide passive ligation of the archwire in the archwire slot. The orthodontic bracket may be configured such that the closure member rotates in a first direction to move the closure member from the opened position to a first closed position, and then further rotated in the first direction to move the closure member from the first closed position to a second closed position. The first direction may be the clockwise or counterclockwise direction. In an alternative embodiment, the closure member rotates in a first direction to move the closure member from the opened position to a first closed position, and rotates in a second direction to move the closure member from the opened position to a second closed position. Moreover, the rotating closure member may include at least two retaining arms for retaining the archwire in the archwire slot. In one embodiment, the rotating closure member may include four retaining arms. In one embodiment, the first and second elements of the retention mechanism cooperate to provide a plurality of positive stops in the rotation of the closure member. The positive stops may correspond to a particular position of the closure member. In this regard, the opened position and/or the at least one closed position of the closure member may correspond to a positive stop of the closure member. In a further embodiment, at least one of the first and second elements is flexible. More particularly, the first element associated with the bracket body may be flexible.

In an exemplary embodiment, the first element of the retention mechanism comprises at least one flexible elongate member coupled to the bracket body, and the second element of the retention mechanism comprises a cam mechanism on the closure member. The flexible elongate member may include a flexible tube or wire. The cam mechanism may comprise a groove in the closure member having a base wall and a pair of side walls extending away from the base wall, wherein at least a portion of the flexible elongate member is positioned in the groove. The flexible elongate member is configured to interact with at least one of the side walls of the groove to prevent the closure member from being separated from the bracket body. Moreover, the flexible elongate member is configured to interact with the base wall of the groove to provide the at least one positive stop in the rotation of the closure member. In one embodiment, the base wall of the groove includes a plurality of flats wherein adjacent flats are separated from each other by an apex or protrusion. The positive stop of the closure member is defined when a flat of the groove confronts the flexible tube. The apex between adjacent flats provides resistance to rotation of the closure member away from the positive stop. In an alternative embodiment, a positive stop of the closure member is defined when the apex engages with a cutout or indentation in the flexible elongate member.

In one embodiment, the first element of the retention mechanism comprises a first flexible elongate member on a first side of the archwire slot and a second flexible elongate member on a second side of the archwire slot. The second element of the retention mechanism comprises a cam mechanism comprising a groove on a first side of the closure member and a cam surface on a second side of the closure member. The first flexible elongate member is configured to interact with the groove to prevent the closure member from being separated from the bracket body, and the second flexible elongate member is configured to interact with the cam surface to provide at least one positive stop in the rotation of the closure member. The first flexible elongate member may be further configured to interact with the groove to provide at least one positive stop in the rotation of the closure member.

In one embodiment, the first element comprises at least one flexible elongate member coupled to the bracket body and the second element comprises a ratcheting mechanism on the closure member. The ratcheting mechanism may be formed in a groove having at least one side wall. The flexible elongate member may interact with the side wall to prevent the closure member from being separated from the bracket body. In one embodiment, the flexible elongate member includes a projection and the ratcheting mechanism includes one or more teeth and one or more troughs. The projection may interact with the teeth to provide the at least one positive stop in the rotation of the closure member. The positive stop may correspond to when the projection is positioned in one of the troughs. Moreover, the number of positive stops may correspond to the number of troughs.

In one embodiment, the flexible elongate member is generally U-shaped and includes a pair of opposing projections. Each projection of the pair of projections may interact with teeth of the ratcheting mechanism to provide the at least one positive stop in the rotation of the closure member.

In one embodiment, the first element comprises at least one flexible elongate member coupled to the bracket body and the second element comprises a carriage mechanism on the closure member. The flexible elongate member may have a slot and the carriage mechanism may include a runner and a ball-like member extending from the runner. The runner may extend into the slot to prevent the closure member from being separated from the bracket body. In one embodiment, the ball-like member is sized to form an interference fit with the slot so as to provide the at least one positive stop in the rotation of the closure member.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
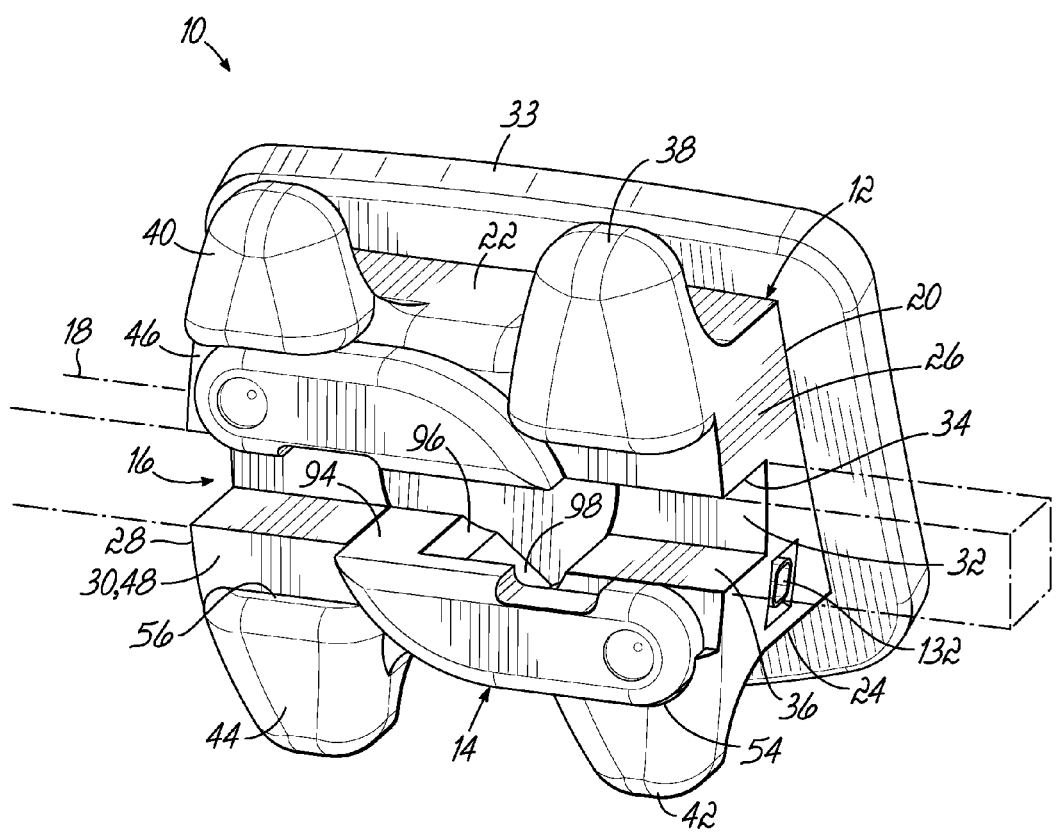
FIG. 1 is a perspective view of a self-ligating orthodontic bracket in accordance with one embodiment of the invention, the closure member shown in the opened position.

Referring now to the drawings, and to FIGS. 1-4 in particular, an orthodontic bracket 10 includes a bracket body 12 and a movable closure member coupled to the bracket body 12. In a preferred embodiment, the movable closure member may include a rotating clip 14 movably coupled with the bracket body 12. The bracket body 12 includes an archwire slot 16 formed therein adapted to receive an archwire 18 (shown in phantom) for applying corrective forces to the teeth. The rotating clip 14 is movable between an opened position (FIGS. 1 and 2) in which the archwire 18 is insertable into the archwire slot 16 without obstruction from the clip 14, and at least one (e.g., preferably at least two) closed position in which the archwire 18 is retained within the archwire slot 16. For example, and as will be explained in more detail below, in the first closed position (FIG. 3), the rotating clip 14 may be configured to actively ligate the archwire 18 in the archwire slot 16, and in the second closed position (FIG. 4), the rotating clip 14 may be configured to passively ligate the archwire 18 in the archwire slot 16. Of course in an alternative embodiment, there may be only a single closed position of the clip 14 or additional closed positions. In any event, the bracket body 12 and rotating clip 14 collectively form a self-ligating orthodontic bracket 10 for use in corrective orthodontic treatments.

The orthodontic bracket 10, unless otherwise indicated, is described herein using a reference frame attached to a labial surface of a tooth on the lower jaw. Consequently, as used herein, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the invention to a particular location or orientation.

When mounted to the labial surface of a tooth carried on the patient's lower jaw, for example, the bracket body 12 has a lingual side 20, an occlusal side 22, a gingival side 24, a mesial side, 26, a distal side 28 and a labial side 30. The lingual side 20 of the bracket body 12 is configured to be secured to the tooth in any conventional manner, such as for example, by an appropriate orthodontic cement or adhesive or by a band around an adjacent tooth. The lingual side 20 may further be provided with a pad 33 defining a bonding base that is secured to the surface of the tooth. The pad 33 may be coupled to the bracket body 12 as a separate piece or element, or alternatively, the pad 33 may be integrally formed with the bracket body 12. The occlusal side 22 of the bracket body 12 includes a pair of tie wings 38, 40 spaced apart in the mesial-distal direction and projecting away from the bracket body 12 in a generally occlusal direction. Similarly, the gingival side 24 of the bracket body 12 includes a pair of tie wings 42, 44 spaced apart in the mesial-distal direction and projecting away from the bracket body 12 in a generally gingival direction.

The bracket body 12 includes a base surface 32 and a pair of opposed slot surfaces 34, 36 projecting labially from the base surface 32 that collectively define the archwire slot 16 extending in a mesial-distal direction from mesial side 26 to distal side 28. The slot surfaces 34, 36 and base surface 32 are substantially encapsulated or embedded within the material of the bracket body 12. The archwire slot 16 of the bracket body 12 may be designed to receive the orthodontic archwire 18 in any suitable manner. As shown in FIGS. 1-5, the bracket body 12 further includes a generally planar support surface 46 extending in a generally gingival-occlusal direction from slot surface 34 and a generally planar support surface 48 extending in a generally gingival-occlusal direction from slot surface 36. As will be discussed in more detail below, the support surfaces 46, 48 are configured to support the rotating clip 14 on the bracket body 12 and are sized so as to allow the rotating clip to move between the opened position and one or more closed positions of the clip 14.

The planar support surfaces 46, 48 are depressed below the labial surfaces of the tie wings 38-44 so as to define gingivally-facing bounding walls 50, 52 on tie wings 38, 40, respectively; and occlussaly-facing bounding walls 54, 56 on tie wings 42, 44, respectively. The area between the bounding walls 50-56 then defines a recessed space configured to receive the rotating clip 14 such that the labial surface of the clip 14 does not extend beyond the labial surface of the tie wings 38-44. More particularly, in one embodiment, the labial surface of the rotating clip 14 may be generally co-planar (e.g., flush) with the labial surface of the tie wings 38-44 so as to facilitate, for example, patient comfort. However, the labial surface of the rotating clip 14 may be below the labial surface of the tie wings 38-44 in an alternative embodiment.

Figure 5:
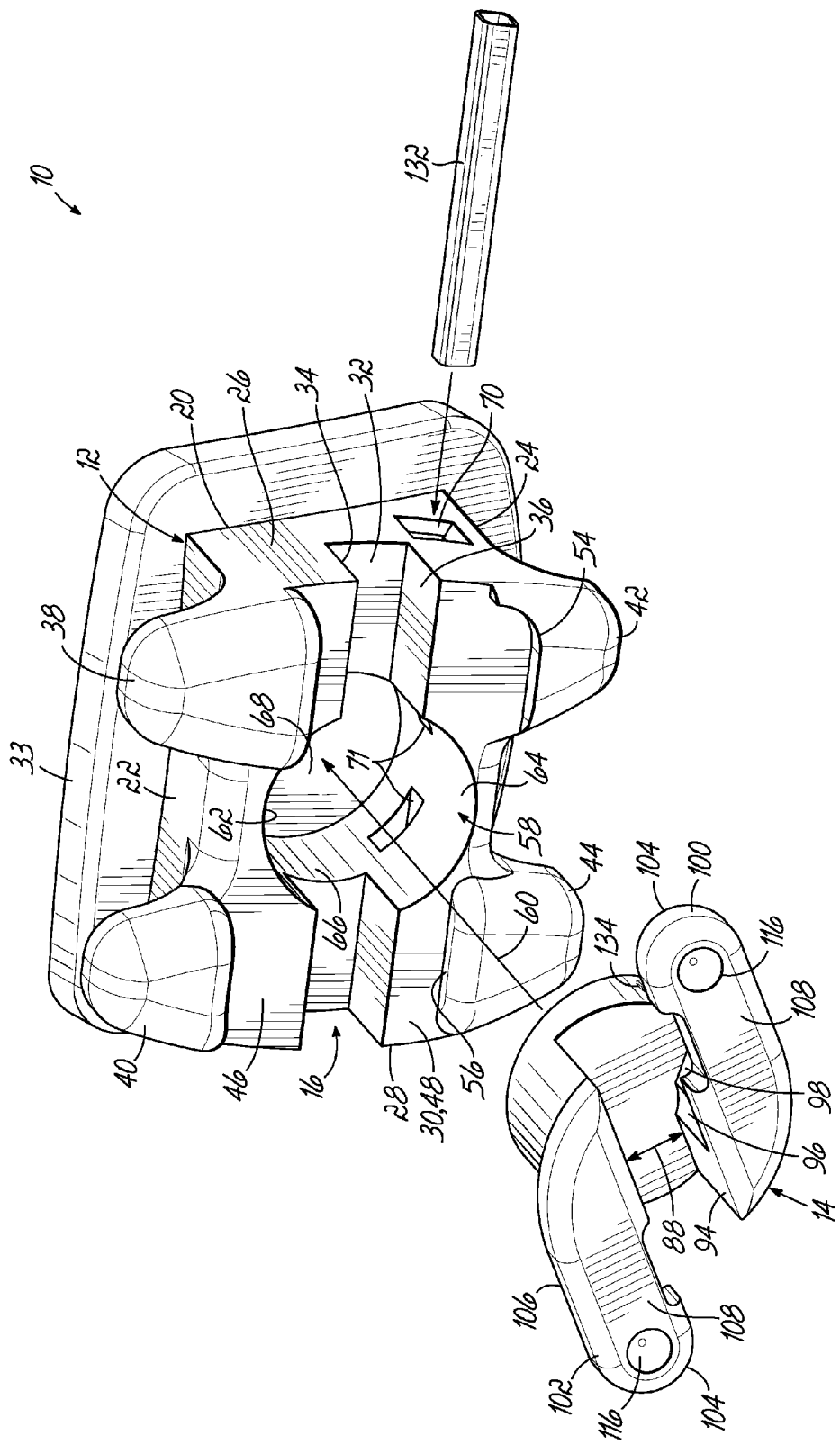
FIG. 5 is a disassembled perspective view of the orthodontic bracket of FIG. 1.

As illustrated in FIG. 5, to receive the rotating clip 14, the bracket body 12 includes a generally cylindrical bore or recess 58 open to the labial side 30 of the bracket body that extends into the bracket body 12 in a generally lingual direction. The cylindrical bore 58 is positioned relative to the bracket body 12 so as to define a central axis 60 extending in the labial-lingual direction and intersecting the archwire slot 16 approximately at its geometric center. As such, the cylindrical bore 58 intersects the archwire slot 16 in a substantially perpendicular manner. The cross dimension of the cylindrical bore 58 is generally greater than the gingival-occlusal height of the archwire slot 16 such that the bore 58 forms a generally arcuate first bore portion 62 on the upper or occlusal side of the archwire slot 16 and having a depth defined by the slot surface 34, and a generally arcuate second bore portion 64 on the lower or gingival side of the archwire slot 16 and having a depth defined by the slot surface 36. Of course, the first and second bore portions 62, 64 are separated from each other by the archwire slot 16. The cylindrical bore 58 penetrates into the bracket body 12 for a depth greater than the depth of the archwire slot 16 so as to define a generally circumferentially continuous third bore portion 66. In an exemplary embodiment, the cylindrical bore 58 is a blind bore, being closed off by a base or bottom surface 68. The depth of the third bore portion 66 may be determined by the distance between the bottom surface 68 and the base surface 32 of the archwire slot 16. While the cylindrical bore 58 has been described herein as a blind bore, it should be recognized that in alternative embodiments, the bore 58 may be a through bore penetrating the bracket body 12 and ultimately being closed off by the pad 33.

As further shown in FIGS. 1-5, the bracket body 12 includes a channel or passageway 70 configured to receive an aspect of a retention mechanism, as will be explained further below, for securing the rotating clip 14 to the bracket body 12. In an exemplary embodiment, the channel 70 is open to at least one of the mesial and distal sides 26, 28 and extends substantially parallel to the archwire slot 16 (e.g., in the mesial-distal direction). For example, in one embodiment, the channel 70 may be open to only one of the mesial or distal sides 26, 28 of the bracket body 12 and be closed off opposite the open side. Alternatively, the channel 70 may be open to both the mesial and distal sides 26, 28 of the bracket body 12 so as to present a through channel. In an exemplary embodiment, the channel 70 penetrates the bracket body 12 so as to be generally positioned below (e.g., lingual) the archwire slot 16 such that the channel 70 does not intersect the archwire slot 16. More particularly, and as illustrated in the figures, the channel 70 may be generally positioned on the gingival side of the archwire slot 16. In an alternative embodiment, however, the channel 70 may be positioned on the occlusal side of the archwire slot 16.

In accordance with an aspect of the invention, the channel 70 is configured to intersect with the cylindrical bore 58 such that the channel 70 and the bore 58 are open to each other, such as at openings 71. More particularly, in an exemplary embodiment, since the channel 70 is generally positioned below the archwire slot 16, the channel 70 intersects with the third bore portion 66 of the cylindrical bore 58. The purpose of the channel 70 as it pertains to retaining the rotating clip 14 to the bracket body 12 will be discussed in more detail below.

Figure 3:
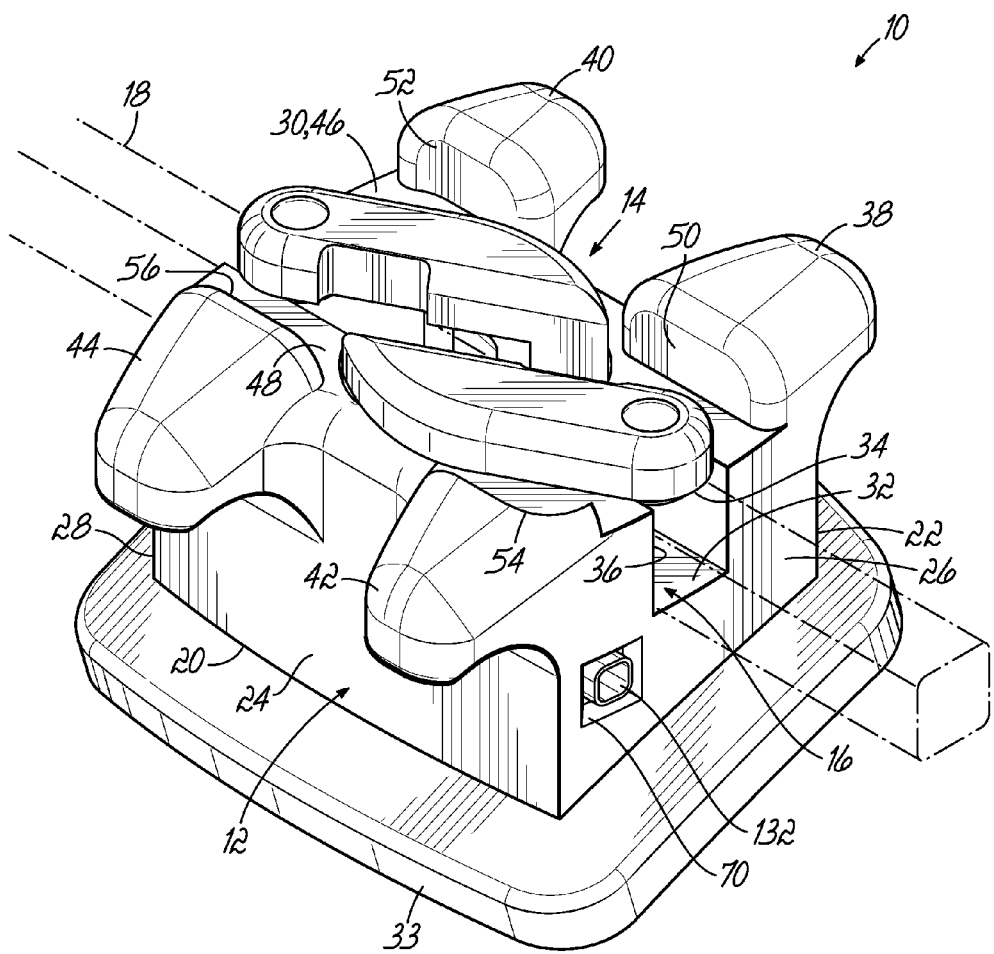
FIG. 3 is a perspective view of the orthodontic bracket of FIG. 1 with the closure member shown in a closed position.
Figure 4:
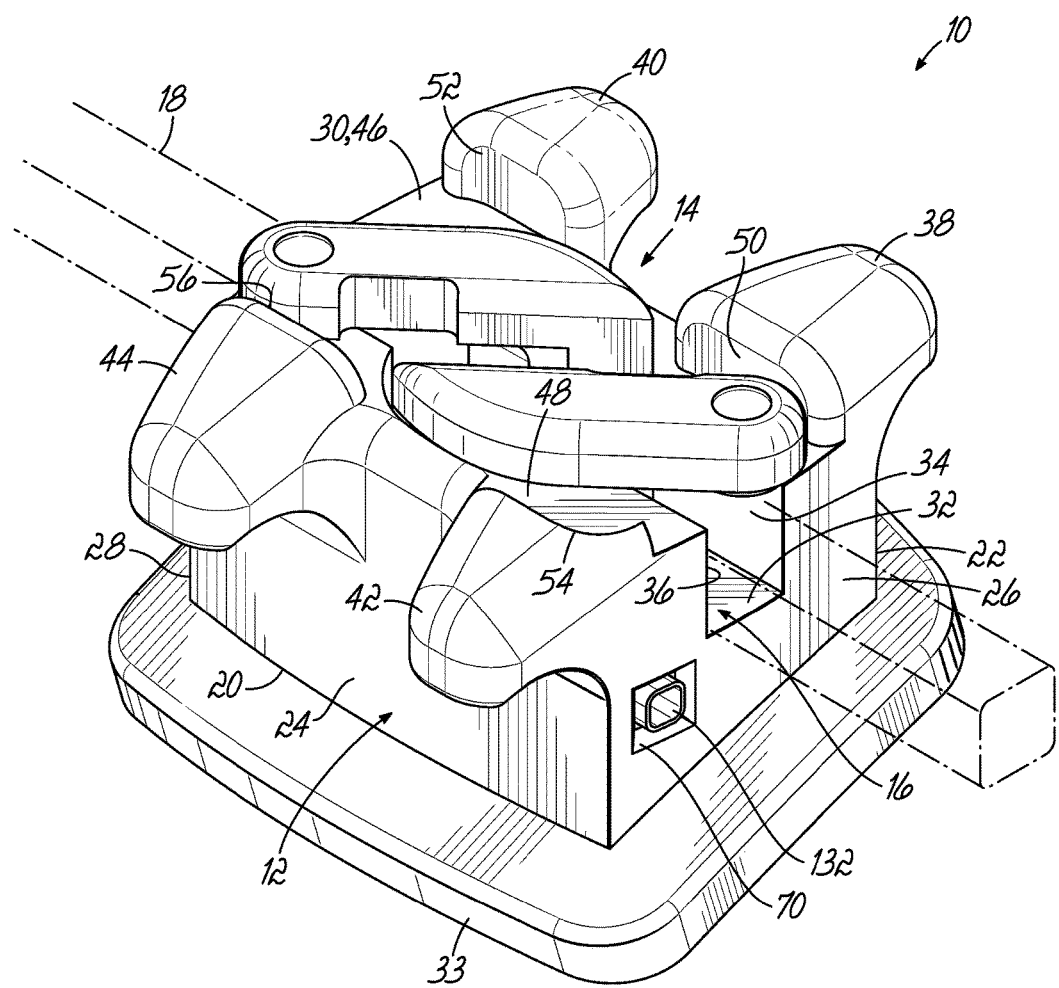
FIG. 4 is a perspective view of the orthodontic bracket of FIG. 1 with the closure member shown in another closed position.
Figure 6:
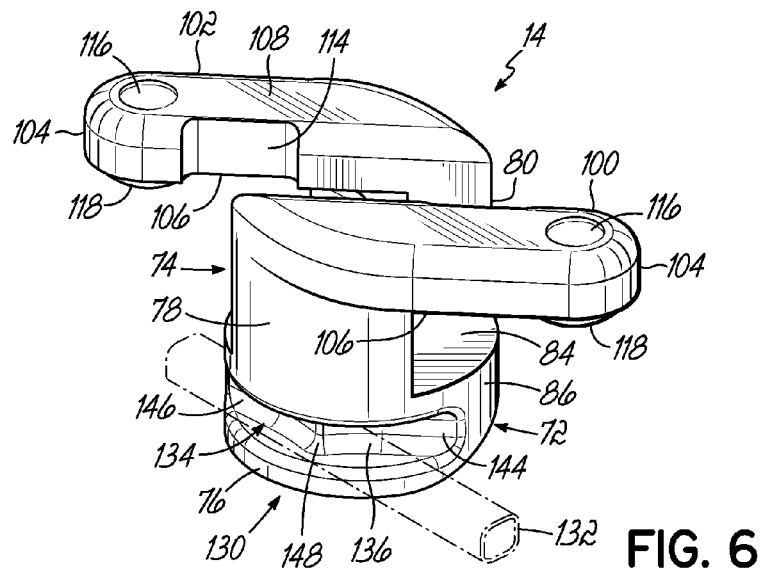
FIG. 6 is a perspective view of a closure member in accordance with an embodiment of the invention.
Figure 6A:
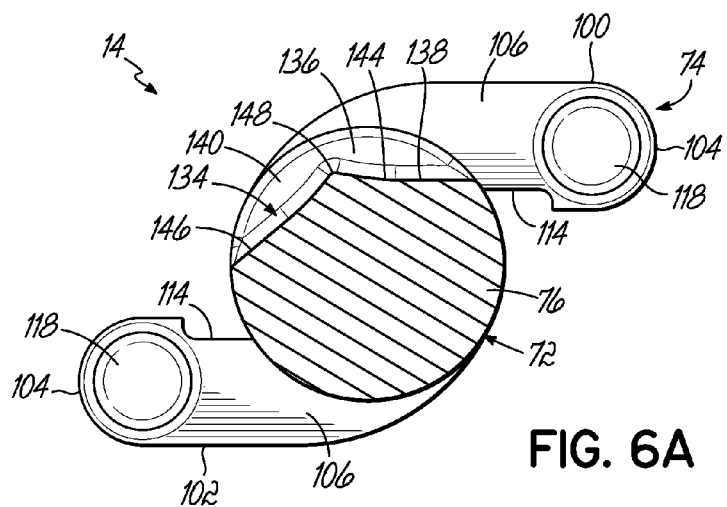
FIG. 6A is a cross-sectional view of the closure member shown in FIG. 6.
Figure 6B:
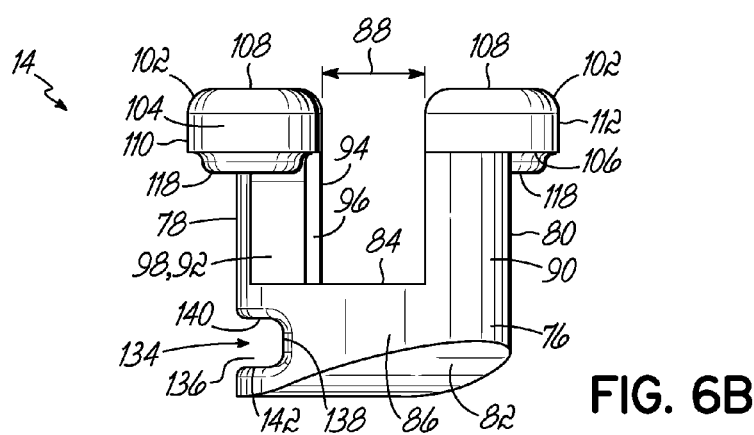
FIG. 6B is a side elevation view of the closure member shown in FIG. 6.

As illustrated in FIGS. 6A-6C, the rotating clip 14 comprises a generally cylindrical retaining portion 72 configured to be received in the cylindrical bore 58 of the bracket body 12, and a ligating portion 74 configured to ligate the archwire 18 (e.g., actively and/or passively) when the clip 14 is in the closed position(s) (FIGS. 3 and 4). In one embodiment, the cylindrical retaining portion 72 includes a generally cylindrical base 76 and a pair of spaced-apart columns or studs 78, 80. The cylindrical base 76 is generally disc-shaped and includes a lower surface 82, an upper surface 84, and a side wall 86 extending therebetween. The cylindrical base 76 is configured to be received in the third portion 66 of the bore 58. In one embodiment, the upper surface 84 may be generally planar and substantially flush with the base surface 32 of the archwire slot 16 when the clip 14 is positioned in the bore 58. However, the lower surface 82 may be generally non-planar (e.g., angled configuration) and shaped to accommodate, for example, a certain prescription of the orthodontic bracket 10 (FIG. 6B). The shape of the cylindrical base 76 is such that the rotating clip 14 may rotate within the cylindrical bore 58 between the opened and closed position without interference between the cylindrical base 76 and a portion of the bore 58 (such as the third bore portion 66). Additionally, the cylindrical base 76 is sized (e.g., cross dimension, diameter) just slightly under the size of the cylindrical bore 58.

The studs 78, 80 generally extend upwardly (e.g., labially) from the upper surface 84 of the cylindrical base 76 in a generally perpendicular manner and are arranged such that there is an opening or gap 88 between the two studs 78, 80. The size of the gap 88 may vary, but is such that when the rotating clip 14 is in the opened position (FIGS. 1 and 2), there is an unobstructed path for the archwire 18 to be inserted into the archwire slot 16 (FIG. 1). Each stud 78, 80 includes an outer surface 90 having a generally arcuate configuration such that the outer surface 90 is smooth and continuous with the side wall 86 (FIG. 6B) of the cylindrical base 76 (e.g., it is an extension of the cylindrical configuration of the base 76). The arcuate outer surface 90 of the studs 78, 80 and configured to generally confront the first and second bore portions 62, 64.

Each stud 78, 80 further includes an inner surface 92 configured to confront the archwire 18 when the orthodontic bracket 10 is assembled. In an exemplary embodiment, the inner surface 92 is specifically designed or contoured so as provide multiple rotational positions of the clip 14 relative to the bracket body 12 (and the archwire slot 16 more specifically) for which the archwire 18 may pass between the two studs 78, 80 without significant interference of being blocked thereby. In this regard, in one embodiment, the inner surface 92 of each of the studs 78, 80 may include a first surface portion 94, an intermediate second surface portion 96, and a third surface portion 98 (FIGS. 1, 5, and 6B). The surface portions 94, 96, 98 on stud 78 are arranged generally opposite to the surface portions 94, 96, 98 of the other stud 80, such that the surface portions 94, 96, 98 on stud 78 generally face surface portions 98, 96, 94 on the other stud 80.

The first surface portion 94 of the inner surface 92 may be configured such that in the opened position of the rotating clip 14, this surface on the studs 78, 80 generally confronts the archwire 18 in the archwire slot 16. By way of example, the surface portions 94 may be generally planar and further configured so as to be generally co-planar with the slot portions 34, 36 of the archwire slot 16 when in the opened position. The second surface portion 96 of the inner surface 92 may be configured such that in one of the closed positions (e.g., the active ligating position), the second surface portions 96 generally confront the archwire 18 in archwire slot 16. In one embodiment, the second surface portions 96 may be generally arcuate. Lastly, the third surface portion 98 of the inner surface 92 may be configured such that in one of the closed positions (e.g., the passive ligating position), the third surface portion 98 of the inner surface 92 may generally confront the archwire 18. By way of example, the surface portions 98 may be generally planar and further configured so as to be generally co-planar with the slot portions 34, 36 of the archwire slot 16 when in a closed position.

Figure 2:
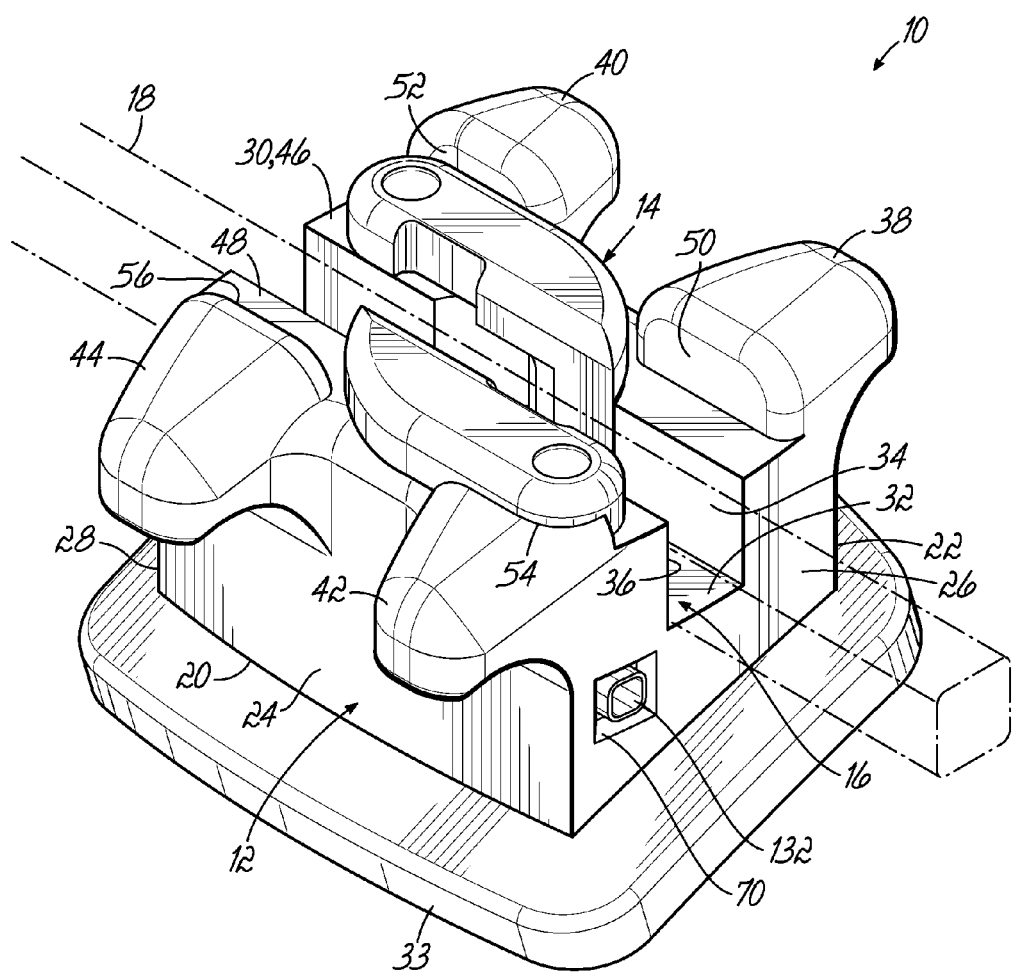
FIG. 2 is another perspective view of the orthodontic bracket of FIG. 1, the closure member also shown in the opened position.

The ligating portion 74 of the clip 14 includes a cantilevered retention arm 100, 102 extending from each of the studs 78, 80 in a transverse manner such that the retention arms 100, 102 are generally parallel to the upper surface 84 of the cylindrical base 76 (FIG. 6B). The retention arms 100, 102 are arranged on their respective studs 78, 80 so as to be directed in opposite directions and to terminate at a free end 104. By way of example, and as illustrated in FIGS. 1 and 2, when the rotating clip 14 is in the opened position, retention arm 100 is generally extending in the mesial direction, and retention arm 102 is generally extending in the distal direction. Each of the retention arms 100, 102 includes a lower surface 106, an upper surface 108, and a side wall 110 extending therebetween. Each of the surfaces 106-110 may be generally planar (except at the free end 104 which may be generally arcuate) and the edges between the surfaces may be radiused so as to provide smooth or contoured edges to the clip 14 in an effort to facilitate patient comfort.

In one embodiment, an inner surface of each of the retention arms 100, 102 may include a notch or cut out 114 and the upper surface 108 of each of the retention arms 100, 102 may include a depression or recess 116 adjacent the free end 104 thereof. The notches 114 and recesses 116 may operate as a tool receptacle for mating with a suitable tool (not shown) configured to facilitate rotation of the clip 14 in a relatively simplified manner. For example, the notches may be configured to receive a portion of the tool to center the tool and to prevent undesirable movement of the tool during use. Furthermore, in an embodiment, the lower surface 106 of each of the retention arms 100, 102 may include an engagement element 118 (FIG. 6A) configured to engage with the archwire 18 when the clip 14 is in an active ligating position. In an exemplary embodiment, the engagement element 118 may include a disc-shaped pad or button on the lower surface 106 of the retention arms 100, 102. The button may be formed from NiTi or other suitable materials for engaging with the archwire 18.

In accordance with an aspect of the invention, the orthodontic bracket 10 includes a retention mechanism, generally illustrated at 130, having multi-functional capabilities in regard to the rotating clip 14. More particularly, the multi-functional retention mechanism 130 is configured to not only movably secure the clip 14 to the bracket body 12 such that the two elements cannot be separated from each other, but also provide an indication of the rotational position of the clip 14 relative to the bracket body 12. In regard to the former point, the retention mechanism 130 is configured to secure the clip 14 to the bracket body 12 such that, for example, the clip 14 cannot be pulled away from the bracket body 12 in the buccal or labial direction. However, while securing the clip 14 to the bracket body 12, the retention mechanism 130 is further configured to permit rotational movements of the clip 14 relative to the bracket body 12 between the opened position and one or more of the closed positions. In regard to the latter point, the retention mechanism 130 is configured to provide one or more positive stops in the rotation of the clip 14 relative to the bracket body 12. As used herein, a positive stop is where there is an interaction between the clip 14 and the bracket body 12 such that a threshold level of force or torque must be applied to the clip 14 in order for the clip to rotate relative to the bracket body 12 in at least one direction (e.g., clockwise or counterclockwise). Of course when the clip 14 is positioned within the cylindrical bore 58 of the bracket body 12, there may a certain amount of friction between the two such that rotating the clip will require a certain amount of force or torque even in the absence of a positive stop feature. The threshold level of force or torque for defining a positive stop is intended to be greater than that required to overcome this type of friction between the clip 14 and bracket body 12.

In accordance with that described above, in an embodiment of the invention, the bracket body 12 includes a first aspect or element and the rotating clip 14 includes a second aspect or element, wherein the first and second elements are configured to interact with each other in a manner that movably (i.e., rotatably) secures the clip 14 to the bracket body 12 and provides at least one positive stop to the rotation of the clip 14 relative to the bracket body 12. In an exemplary embodiment, the first and second elements are configured so as to provide a plurality of positive stops to the rotation of the clip 14 relative to the bracket body 12. When the clip 14 is in one of the positive stop positions, a threshold force or moment must be applied to the clip 14 in order to rotate the clip 14 away from the positive stop position in at least one direction. The threshold force or moment is defined at least in part by the interaction between the first and second elements. Once the threshold force or torque is overcome, the clip 14 will rotate in the direction of the applied force or torque.

Figure 7A:
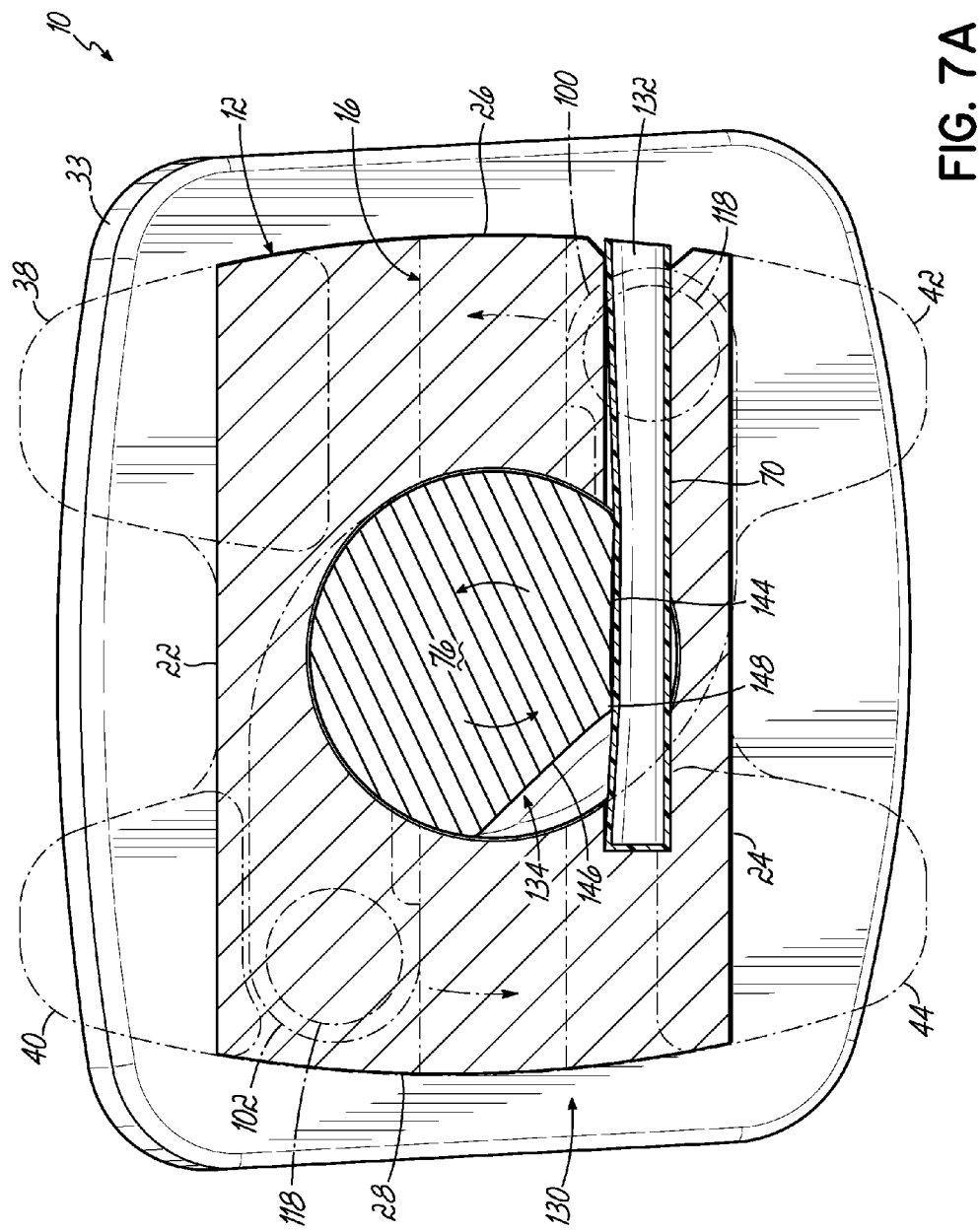
FIG. 7A is a cross-sectional view of the orthodontic bracket of FIG. 1 when the closure member is in the opened position.
Figure 7B:
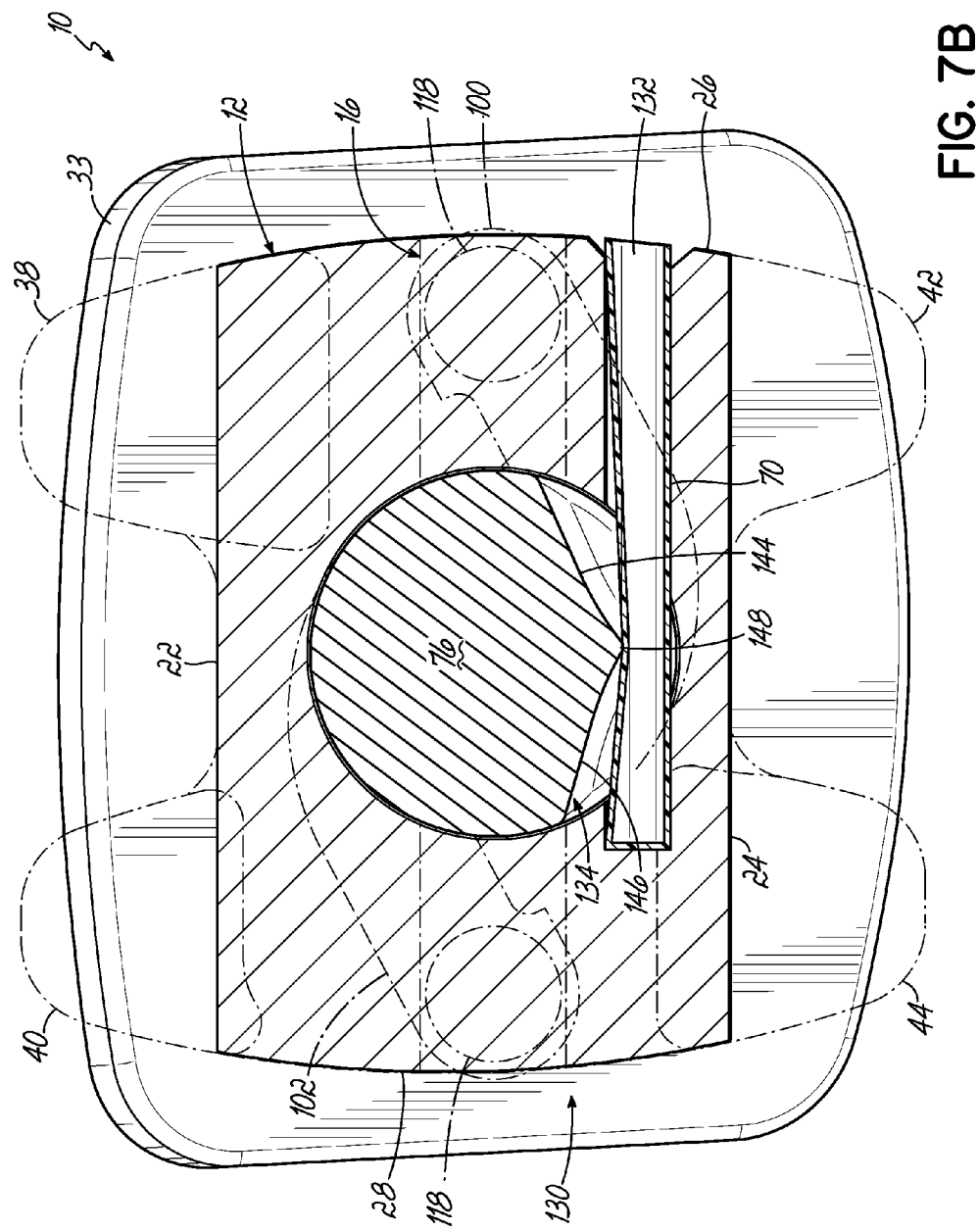
FIG. 7B is a cross-sectional view of the orthodontic bracket of FIG. 1 when the closure member is in a closed position.
Figure 7C:
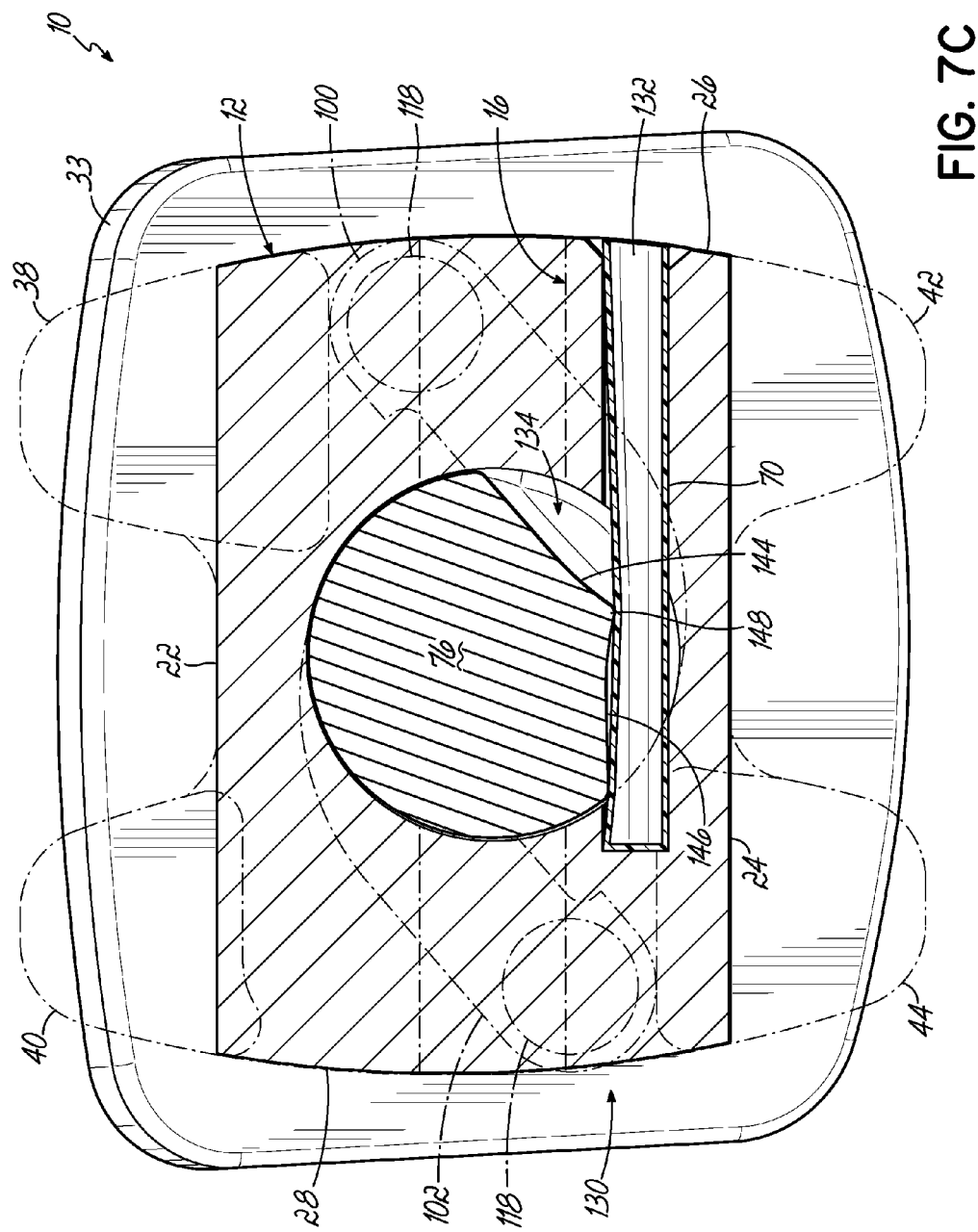
FIG. 7C is a cross-sectional view of the orthodontic bracket of FIG. 1 when the closure member is in another closed position.

In an exemplary embodiment and as illustrated in FIGS. 7A-7C, the retention mechanism 130 includes an elongate member coupled to the bracket body 12. As illustrated in the figures, the elongate member may be configured to be positioned in the channel 70 of the bracket body 12 such that at least a portion of the elongate member intersects with the cylindrical bore 58, such as through openings 71. In one embodiment, the elongate member may be configured as an elongate tube 132 configured to be flexible or deformable to provide a spring-like biasing feature to the elongate member. For example, in one embodiment, the elongate tube 132 may be a hollow tube formed from NiTi, other superelastic materials, or other materials having some flexible or deformable properties. Other configurations for the elongate member, such as a solid tube, partial tube, hollow or solid wires may also be possible (several of which are described below). The cross-sectional shape of the elongate tube 132 may vary. By way of example, the cross-sectional shape of the elongate tube 132 may be circular, square, rectangular, or other suitable shape. Moreover, the cross-sectional shape of the elongate tube 132 and the channel 70 may generally correspond to each other such that the elongate tube 132 may be effectively received in the channel 70 and be secured to the bracket body 12. As noted above, the elongate tube 132 is configured to interact with the rotating clip 14. In this regard, the first aspect of the retention mechanism 130 generally described above includes the elongate tube 132.

Further, the retention mechanism 130 includes a cam mechanism 134 formed in or otherwise coupled to the rotating clip 14. As will be explained in further detail, the cam mechanism 134 is configured to interact with the elongate tube 132 to provide the functions described above, and thus the second aspect of the retention mechanism 130 generally described above includes the cam mechanism 134. In an exemplary embodiment, the cam mechanism 134 may be formed as part of the rotating clip 14. More particularly, the cam mechanism 134 may be formed in the cylindrical base 76 of the clip 14. In this regard and in an exemplary embodiment, the cam mechanism 134 may include a notch or groove 136 formed in the side wall 86 of the cylindrical base 76. The groove 136 includes a floor or base wall 138 and a pair of spaced-apart bounding side walls 140, 142 extending above the base wall 138 on either side thereof. The base wall 138 may not be planar across the full extent, but include a plurality of flats in an end-to-end arrangement, wherein each flat is generally planar. By way of example, and as illustrated, in an exemplary embodiment, the base wall 138 may include two flats 144, 146 which meet at an interface that defines a protrusion or apex 148 formed by an angled relationship between adjacent flats (FIG. 6A). It should be realized that in alternative embodiments, additional flats may be included, depending on the number of positive stops desired in the rotation of the clip 14.

When the rotating clip 14 is positioned within the cylindrical bore 58 of the bracket body 12 and the orthodontic bracket 10 is assembled, a portion of the elongate tube 132 is positioned within the groove 136 in the base 76 of the clip 14 (FIG. 6). When so positioned, the clip 14 is prevented from being separated from the bracket body 12. In this regard, should the clip 14 be pulled away from the bracket body 12, such as in the labial direction, the lower bounding wall 142 of the groove 136 would contact the elongate tube 132 and prevent movement of the clip 14 away from the bracket body 12. Accordingly, through the interaction of the elongate tube 132 and the groove 136, and more particularly the bounding walls 140, 142 thereof, the clip 14 is secured to the bracket body 12. It should be noted, however, that the interaction between the elongate tube 132 and the bounding walls 140, 142 of the groove 136 do not restrict or otherwise prevent rotation of the clip 14 relative to the bracket body 12.

In addition to the above, the elongate tube 132 is configured to interact with the groove 136, and more particularly, the base wall 138 thereof to provide at least one, and preferably a plurality of positive stops to the rotation of the clip 14 relative to the bracket body 12. In this regard, in a certain position of the clip 14 relative to the bracket body 12, one of the flats 144, 146 may confront the elongate tube 132 such that there is a mating relationship between the flat and the elongate tube 132. For example, the flat and a surface of the elongate tube 132 may generally represent parallel planes in abutting relation or near abutting relation to each other. Due to the geometry of the base wall 138 of the groove 136, when the clip 14 is rotated, the apex 148 between the flats 144, 146 will come into contact with the elongate tube 132, and thus resist further rotation of the clip 14. However, with a sufficiently high force or torque applied to the clip 14, the apex 148 will flex or deform the elongate tube 132 so as to allow the apex 148 to pass by the elongate tube 132 as the clip 14 rotates. When the apex 148 passes by the elongate tube 132, the other flat is then in confronting relation to the elongate tube such that there is a mating relationship between the flat and the elongate tube 132. For example, the flat and a surface of the elongate tube 132 may generally represent parallel planes in abutting relation or near abutting relation to each other. Thus, a positive stop is provided in the rotation of the clip 14 when one of the flats 144, 146 of the cam mechanism 134 generally confronts the elongate tube 132. Of course, the retention mechanism 130 may be designed such that the positive stops may correspond to one of the opened and/or closed positions, as will be explained below.

Operation of the orthodontic bracket 10 will now be described. For purposes of discussion, the starting point will be the opened position of the clip 14 as illustrated in FIGS. 1, 2 and 7A. In the opened position, the retention arms 100, 102 are positioned so as to overlie and extend along the support surfaces 46, 48 of the bracket body, respectively, and thus do not extend over the opening to the archwire slot 16. Additionally, the openings or gaps 88 between the studs 78, 80 of the clip 14 are generally aligned with the archwire slot 16. As such, and as illustrated in FIG. 1, there is an unimpeded path between the exterior of the bracket 10 and the archwire slot 16 so as to allow the archwire 18 to be inserted therein. Additionally, when in the opened position, one of the flats 144 is in confronting relation with the elongate tube 132 such that the opened position represents one of the positive stops, and the clip 14 cannot be rotated away from the opened position until a threshold force/torque is applied to the clip 14 (FIG. 7A).

Once the archwire 18 is seated in the archwire slot 16, the rotating clip 14 may be moved to a closed position. In one embodiment, the orthodontic bracket 10 may be configured to have two closed positions, one closed position providing active ligation of the archwire 18 and the other closed position providing passive ligation of the archwire 18. In this regard and as illustrated in FIGS. 7A and 7B, when a threshold force/torque is applied to the rotating clip 14, such as via a suitable tool that engages the tool receptacles 116 on the retention arms 100, 102 of the clip 14, the clip 14 may rotate counterclockwise such that the retention arms 100, 102 move over the archwire slot 16 so as to retain the archwire 18 therein. As illustrated in FIGS. 3 and 7B, as the retention arms 100, 102 move over the archwire slot 16, the engagement elements 118 on the lower surface 106 of the arms 100, 102 engage the archwire 18 so as to impose a force thereon toward the base surface 32 of the archwire slot 16. This represents an active ligation arrangement of orthodontic treatment. In one embodiment, the active ligation position of the clip 14 may not represent a positive stop position of the clip 14. In this regard, in one embodiment, when the clip 14 is in the active ligation position, the apex 148 in the base wall 138 of the groove 136 may be engaged with the elongate tube 132 (e.g., approximately at the midpoint of the passage of the apex 148 past the elongate tube 132, see FIG. 7B). In this case, the resistance to unintentional or accidental rotation of the clip 14 away from the active ligation position is provided by the additional frictional forces between the clip 14 and the archwire 18.

In accordance with an exemplary embodiment and as illustrated in FIGS. 7B and 7C, further rotation of the clip 14 relative to the bracket body 12 in the counterclockwise direction causes the retention arms 100, 102 to move further over the archwire slot 16. The rotation is sufficient to cause the free ends 104 of the retention arms 100, 102 to engage the opposite support surface 46, 48. More particularly, the free ends 104 of the retention arms 100, 102 are flexed upwardly such that the engagement elements 118 on the lower surface 106 of the arms 100, 102 no longer engage the archwire 18, but engage the support surfaces 46, 48 on the opposite side of the archwire slot 16. This configuration then provides a passive ligation arrangement. In one embodiment, when the clip 14 is in the second closed position, i.e, the passive ligating position, the other flat 146 is in confronting relation with the elongate tube 132 such that this closed position represents one of the positive stops, and the clip 14 cannot be rotated away from the closed position (e.g., back in the clockwise direction) until a threshold force/torque is applied to the clip 14 (FIG. 7C).

As described above, the orthodontic bracket 10 includes a retention mechanism 130 having a multi-functional capability. More particularly, the retention mechanism 130 secures the rotating clip 14 to the bracket body 12 such that the clip 14 is not separable from the bracket body 12 during use. Additionally, the retention mechanism 130 secures the clip 14 to the bracket body 12 so as to permit rotation of the clip between its opened and closed positions. Furthermore, the retention mechanism 130 provides at least one and preferably a plurality of positive stops to the rotation of the clip 14 relative to the bracket body 12. Providing these positive stops may provide an orthodontist a tactile or audible indication that the clip is an opened and/or closed position. The positive steps also aid in preventing or reducing accidental or unintentional movements of the clip. Of particular benefit is that the same retention mechanism provides both of these functions.

There are a number of alternative embodiments which remain within the scope and spirit of the invention described above. By way of example, the orthodontic bracket 10 shown above was described as rotating the clip 14 in the counterclockwise direction to move the clip from the opened position to the first closed position and then to the second closed position. In an alternative embodiment, the retention arms 100, 102 may be reversed relative to that shown in FIGS. 1-4 such that to move the clip 14 from the opened position to the first closed position and then to the second closed position, the clip would be rotated in the clockwise direction. In a further alternative embodiment, there could be four retention arms associated with the clip, similar to that described in U.S. Pat. No. 8,162,660 In such an embodiment, the orthodontic bracket may be closed and placed in an active ligation arrangement by rotating the clip in a first direction (clockwise or counterclockwise), or closed and placed in a passive ligation arrangement by rotating the clip in a second opposite direction.

Figure 8:
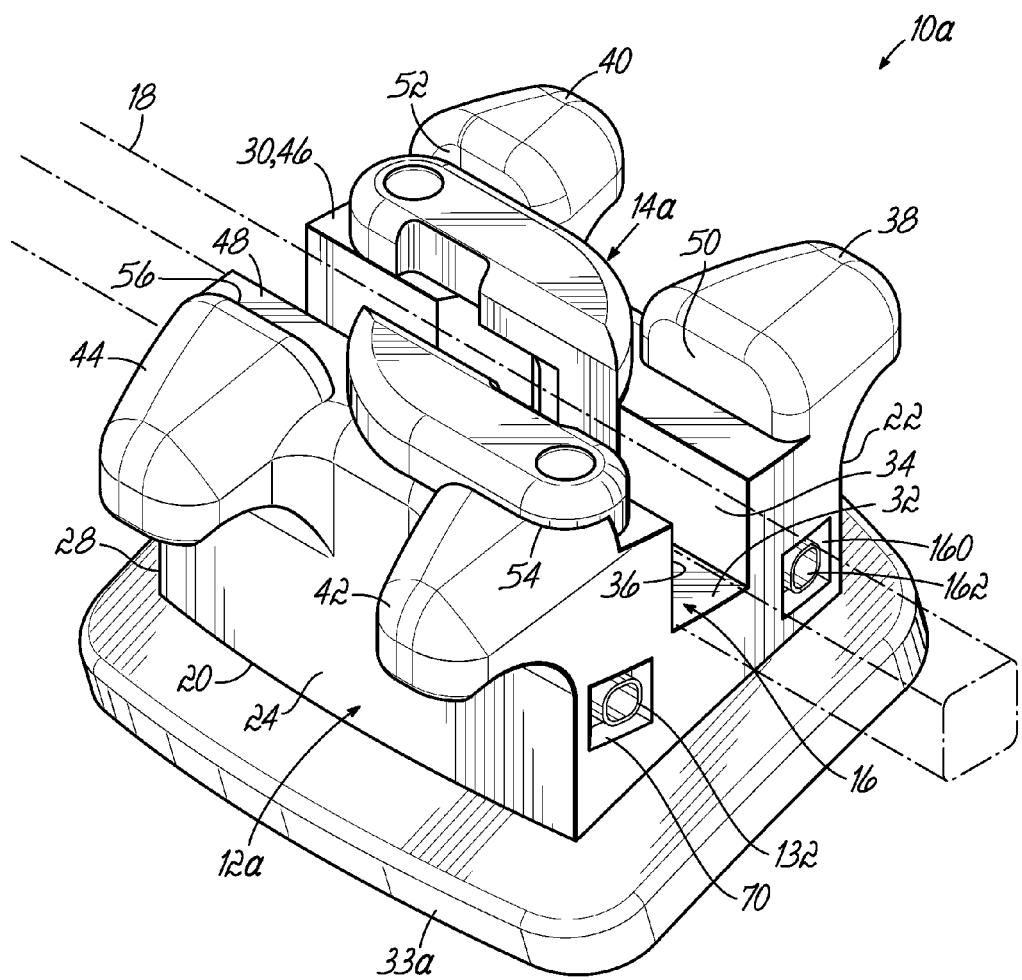
FIG. 8 is a perspective view of a self-ligating orthodontic bracket in accordance with a second embodiment of the invention, the closure member shown in the opened position.
Figure 9A:
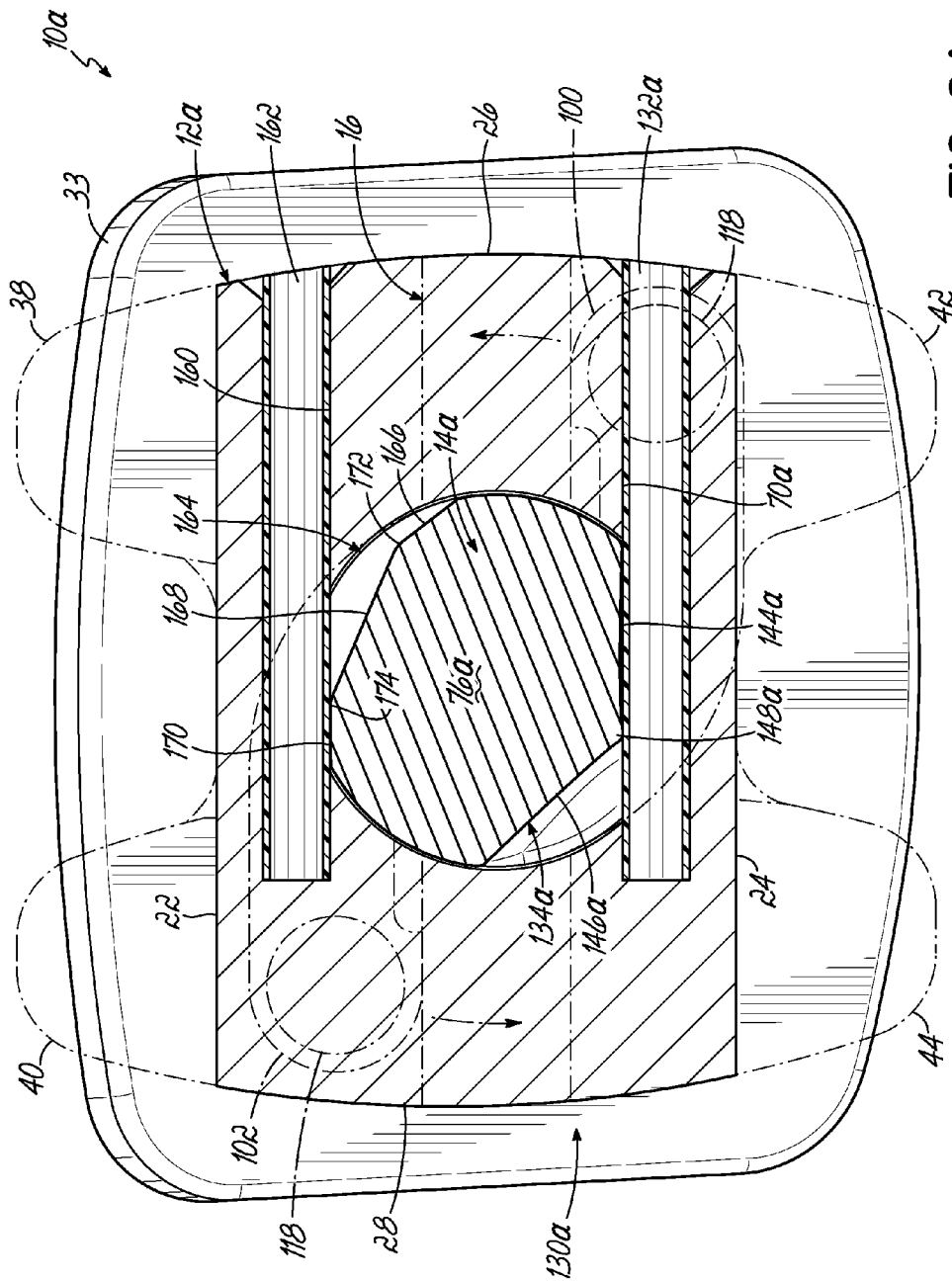
FIG. 9A is a cross-sectional view of the orthodontic bracket of FIG. 8 when the closure member is in the opened position.
Figure 9B:
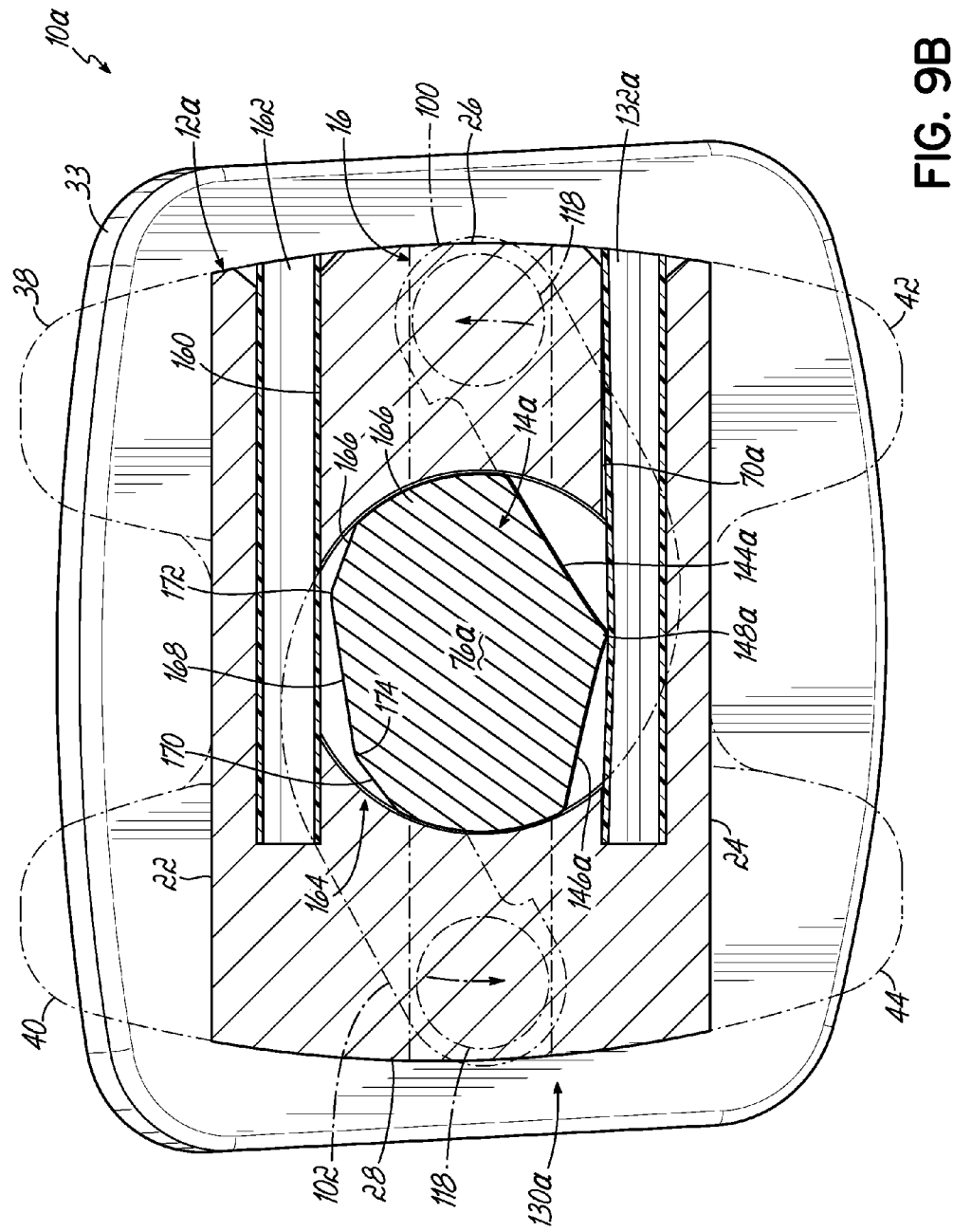
FIG. 9B is a cross-sectional view of the orthodontic bracket of FIG. 8 when the closure member is in a closed position.
Figure 9C:
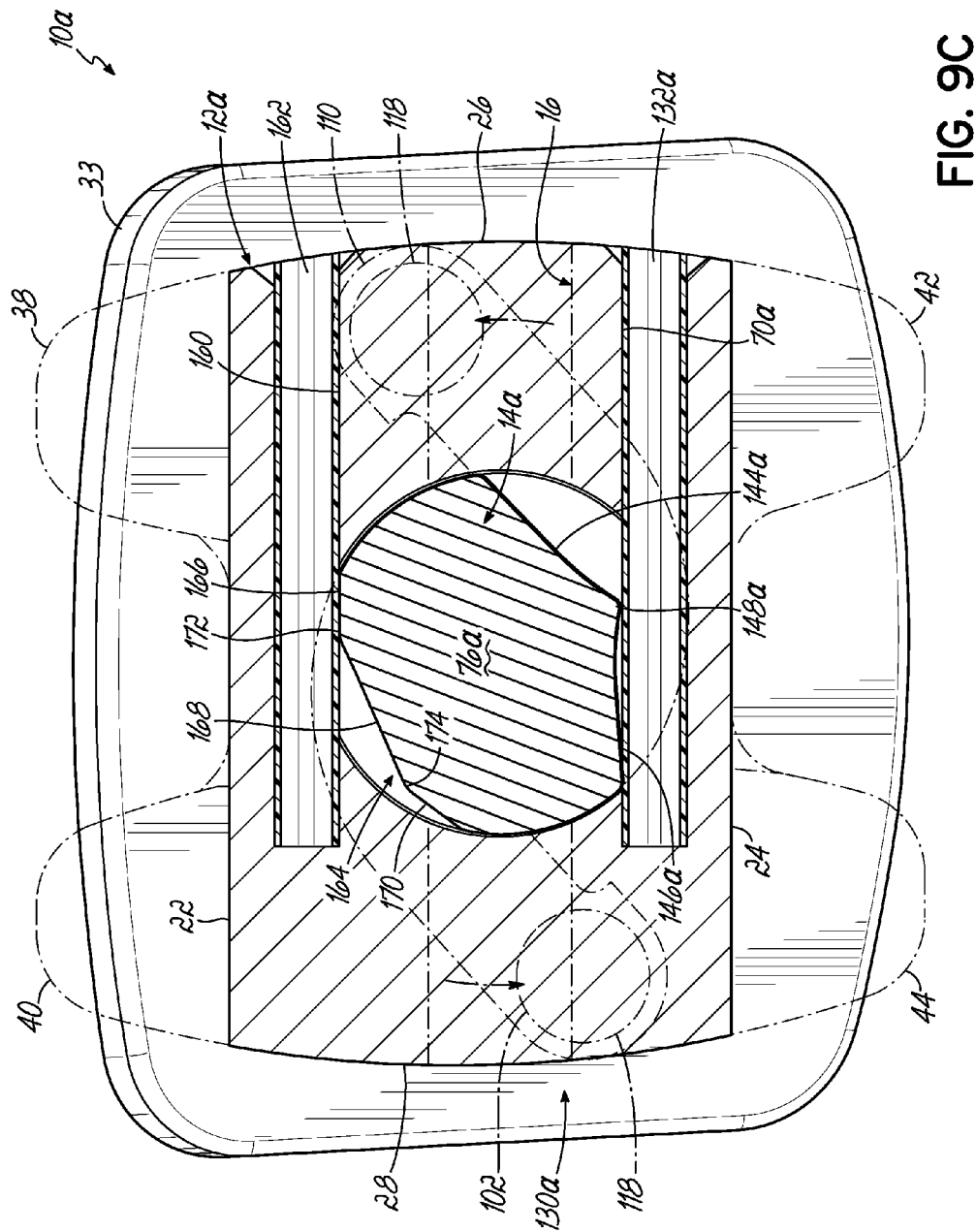
FIG. 9C is a cross-sectional view of the orthodontic bracket of FIG. 8 when the closure member is in another closed position.
Figure 9D:
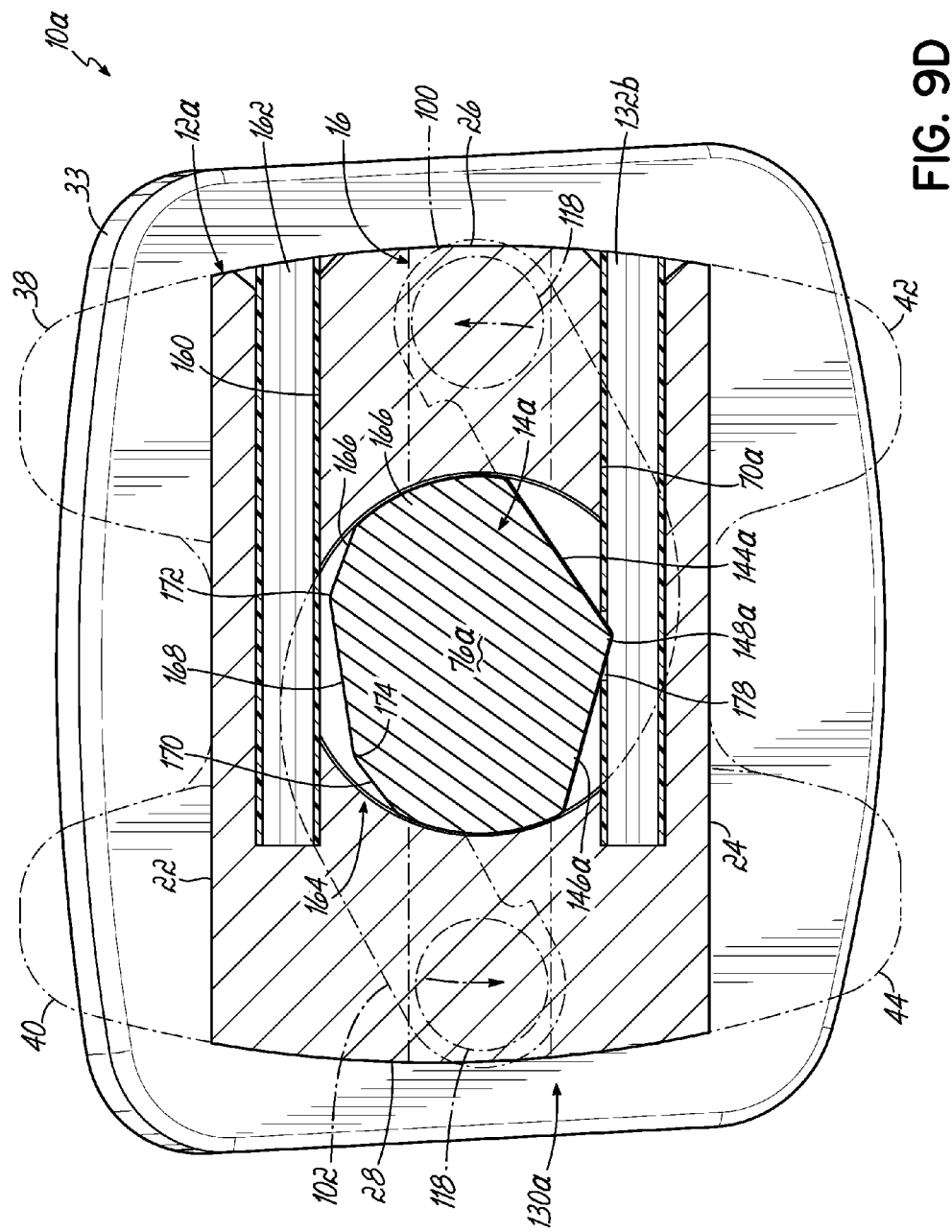
FIG. 9D is a cross-sectional view of an orthodontic bracket in accordance with an alternative embodiment.
Figure 10:
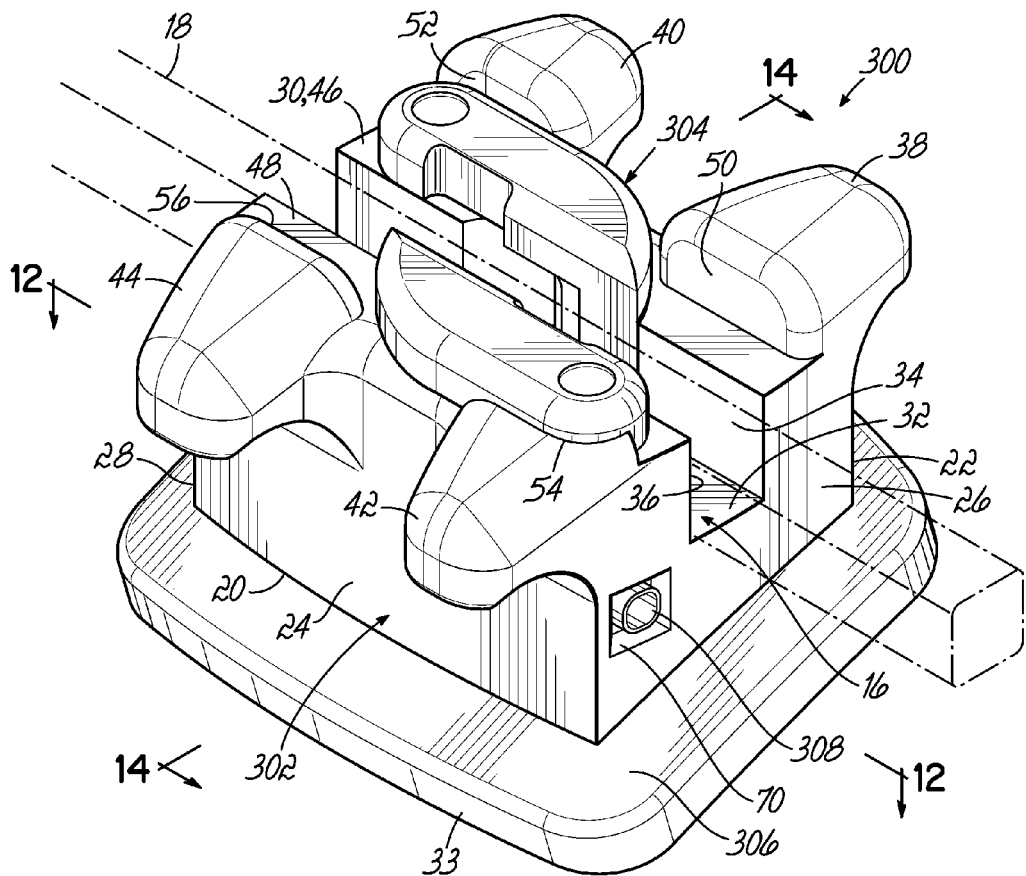
FIG. 10 is a perspective view of a self-ligating orthodontic bracket in accordance with one embodiment of the invention, the closure member shown in the opened position.

In still a further alternative embodiment, as illustrated in FIGS. 8-9C, in which features similar to those in FIGS. 1-7C have the same reference number but suffixed with an "a", the orthodontic bracket 10a, and more particularly the retention mechanism 130a may include a second channel 160 positioned on the opposite side of the archwire slot 16 and a second elongate tube 162 positioned therein. The second channel 160 and the elongate tube 162 may be similar to that described above for channel 70 and elongate tube 132. Similar to the above, the second elongate tube 162 is configured to interact with the clip 14a to perform at least one of the functions described above. In this regard, and in one embodiment, in addition to the groove 136a described above, the cam mechanism 134a on the cylindrical base 76a of the clip may include a cam surface 164 having a plurality of flats 166, 168, 170 separated by apexes 172, 174. The flats 166, 168, 170 may be configured to interact with the second elongate tube 162 to define positive stop positions in the rotation of the clip 14a similar to that described above. By way of example, the flats 166, 170 may be configured to be in confronting relationship with the elongate tube 162 when the flats 144a, 146a are in confronting relationship with the elongate tube 132, respectively. This may correspond, for example, to when the clip 14a is in the opened position and the second closed position. Moreover, the flat 168 may be configured to be in confronting relation with the elongate tube 162 when the rotating clip 14a is in the first closed position. In this regard, the interaction between the cam surface 164 and the elongate tube 162 may provide a positive stop to the rotating clip when in the first closed position.

While in the embodiments described in FIGS. 1-9C, the flats of the cam mechanism were in abutting relation to the elongate tube when in the positive stop position and the apex between the flats provided the resistance to rotation, in an alternative embodiment, a positive stop position may be provided when the apex engages the elongate tube. In this regard and as illustrated in FIG. 9D, in which like reference numerals refer to like features in FIGS. 8-9C, the elongate tube 132b may include a cutout 178 in the portion of the elongate tube 132b that faces the cam mechanism 134a. As the clip 14a is rotated, the apex 148a may initially engage the elongate tube 132b and start flexing the tube. Similar to the above, this engagement provides some resistance to rotation. However, as the clip 14a continues rotate, the apex 148a encounters the cutout 178 in the elongate tube 132b and snaps into a positive stop position. This snap may provide an audible indication that the clip 14a is in a positive stop position (e.g., an active ligation position). The flats 144a, 146a of the cam mechanism 134a may engage the edges of the cutout 178 therefore providing a resistance to rotation of the clip 14a away from this positive stop position. However, with a threshold level of force of moment, the clip 14a may be rotated such that the apex 148a passes out of the cutout 178 and a flat is again in abutting relation to the elongate tube 132b. It should be realized that instead of a cutout, in an alternative embodiment the elongate tube 132b may include an indentation (e.g., a v-shaped indentation) in a portion thereof configured to receive the apex 148a of the cam mechanism 134a in a similar manner as described above.

In one alternative embodiment, and with reference to FIGS. 10-12B in which like reference numerals refer to like elements throughout the figures, an orthodontic bracket 300 includes a bracket body 302 similar to the bracket body 12 and a rotating clip 304 similar to the rotating clip 14, described above, but differing in that a retention mechanism generally indicated at 306 has an alternative structural configuration than the retention mechanism 130 described above and shown in FIGS. 1-9C. While differing in structural configuration from the retention mechanism 130, the retention mechanism 306 has the same functions. That is, for example, to not only movably secure the clip 304 to the bracket body 302 such that the two elements cannot be separated, but also provide an indication of the rotational position of the clip 304 relative to the bracket body 302.

In regard to the former point, the retention mechanism 306 is configured to secure the clip 304 to the bracket body 302 such that, for example, the clip 304 cannot be pulled away from the bracket body 302 in the buccal or labial direction. While securing the clip 304 to the bracket body 302, the retention mechanism 306 is further configured to permit rotational movements of the clip 304 relative to the bracket body 302 between the opened position and one or more of the closed positions. In regard to the latter point, the retention mechanism 306 is configured to provide one or more positive stops in the rotation of the clip 304 relative to the bracket body 302.

In accordance with the embodiment described above, in one embodiment of the invention, and similar to the embodiments described above with reference to FIGS. 1-9C, the bracket body 302 includes a first aspect or element and the rotating clip 304 includes a second aspect or element, wherein the first and second elements are configured to interact with each other in a manner that movably (i.e., rotatably) secures the clip 304 to the bracket body 302 and provides at least one positive stop to the rotation of the clip 304 relative to the bracket body 302. The first and second elements are configured to provide a plurality of positive stops to the rotation of the clip 304 relative to the bracket body 302. When the clip 304 is in one of the positive stop positions, a threshold force or moment must be applied to the clip 304 to rotate the clip 304 away from the positive stop position in at least one direction. The threshold force or moment is defined at least in part by the interaction between the first and second elements.

Figure 12A:
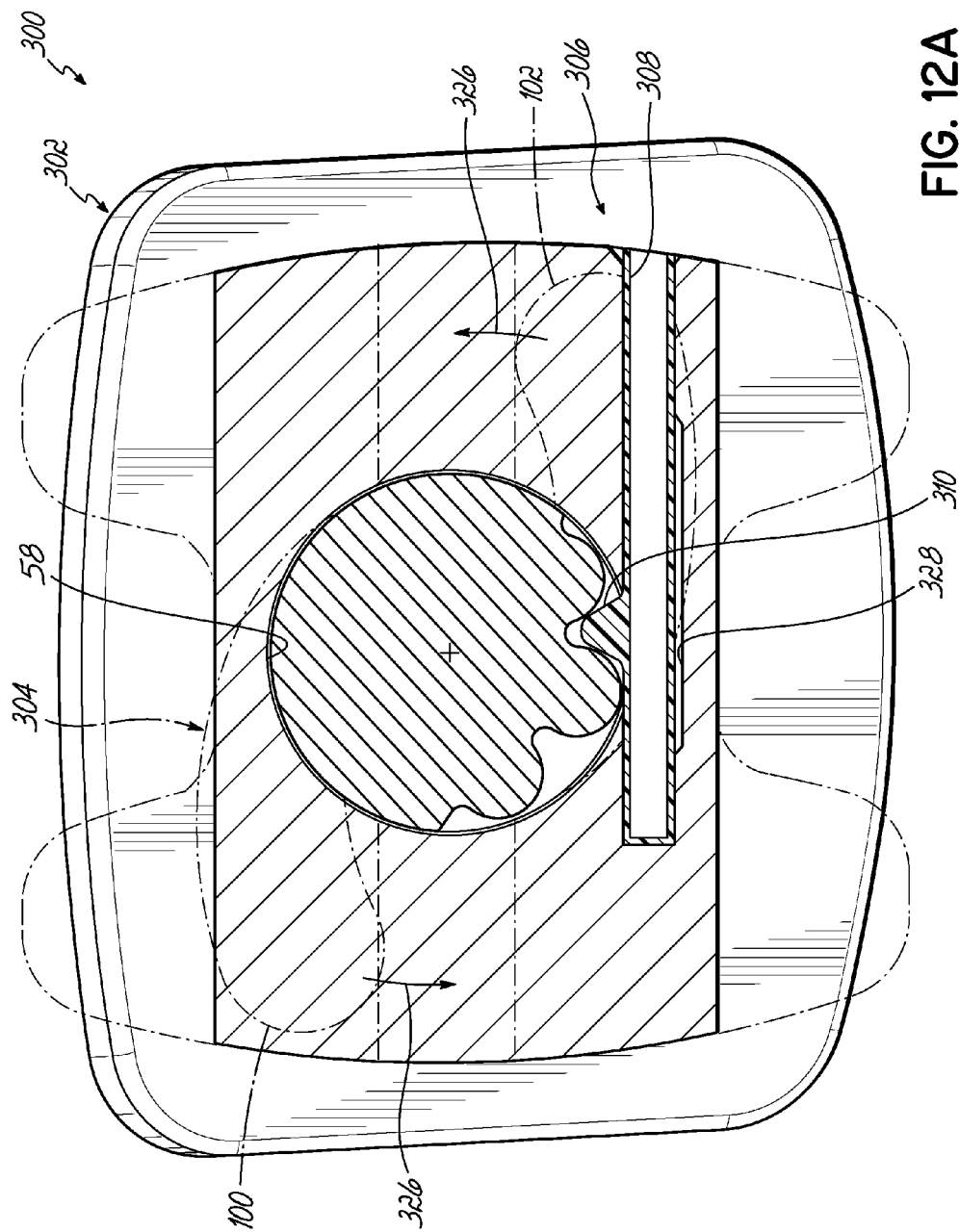
FIG. 12A is a cross-sectional view of the orthodontic bracket of FIG. 10 taken along section line 12-12 when the closure member is in the opened position.

In one embodiment, the retention mechanism 306 includes an elongate tube 308 coupled to the bracket body 302 in the channel 70. At least a portion of the elongate tube 308 intersects with the cylindrical bore 58. This is best shown in FIG. 12A. In one embodiment, the elongate tube 308 is flexible or elastically deformable. For example, in one embodiment, the elongate tube 308 may be a hollow tube formed from NiTi, other superelastic materials, or other materials having some flexible or elastic properties. The shape of the elongate tube 308 includes a bump or wedge 310 that generally extends away from the axis of the tube 308, and when inserted into the channel 70 projects into the cylindrical bore 58. In this manner, the elongate tube 308 interacts with the rotating clip 304 via the wedge 310. It will be appreciated that the wedge 310, while shown as a symmetrical projection, need not be symmetrical. As is described below, the shape of the wedge 310 may determine the threshold force needed to rotate the rotating clip 304 from a positive stop. In this regard, the first aspect of the retention mechanism 306 includes the elongate tube 308. Further, while the elongate tube 308 is shown as having a hollow tubular configuration, embodiments of the invention are not limited to hollow tubes as the retention mechanism may include other configurations, such as, a wire (shown in FIGS. 13C and 13D) having one or more preformed bends therein.

Figure 11:
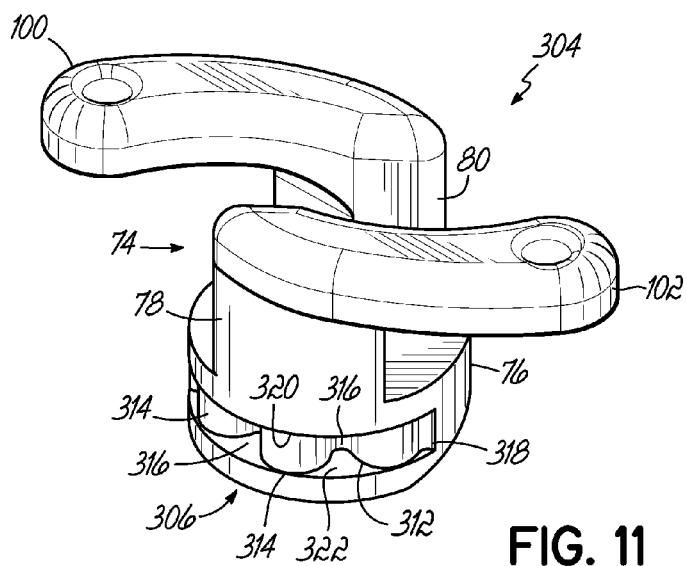
FIG. 11 is a perspective view of a closure member in accordance with an embodiment of the invention.

Further, and with reference to FIG. 11, the retention mechanism 306 includes a ratcheting mechanism 312 formed in or otherwise coupled to the rotating clip 304. As will be explained in further detail, the ratcheting mechanism 312 interacts with the elongate tube 308 to provide the functions described above, and, thus, the second aspect of the retention mechanism 306 includes the ratcheting mechanism 312. In one embodiment, the ratcheting mechanism 312 may be formed as part of the rotating clip 304. More particularly, the ratcheting mechanism 312 may be formed in the cylindrical base 76 of the clip 304.

In this regard, in one embodiment, the ratcheting mechanism 312 includes one or more teeth 314 separated by notches or troughs 316. The ratcheting mechanism 312 is recessed into the side wall 86 of the cylindrical base 76 in a groove 318 defined by a pair of spaced-apart bounding side walls 320, 322 on either side of the notches 316. The crests or lands of the teeth 314 may be coplanar with the surface of the cylindrical base 76, as shown. Alternatively, the teeth 314 may be recessed slightly below the surface of the cylindrical base 76 so that the lands of the teeth 314 are recessed circumferentially within the periphery of the sidewall 86 of the rotating clip 304. By way of example, and as illustrated, in one embodiment, the groove 318 may include three teeth 314 separated by two notches 316. It should be realized that additional teeth and notches may be included depending on the number of positive stops desired in the rotation of the clip 304. In addition, while the teeth 314 are shown as having a generally arcuate configuration, embodiments of the present invention are not limited thereto, as other configurations may be utilized where it is desirable to modify the threshold force required to move the rotating clip 304 between any two positions. Further along these lines, the teeth 314 need not be symmetrical with respect to one another as it will be appreciated that different threshold forces may be desired for each positive stop and the shape and size of the individual teeth 314 may be modified to achieve a particular threshold force for a particular positive stop.

Figure 12B:
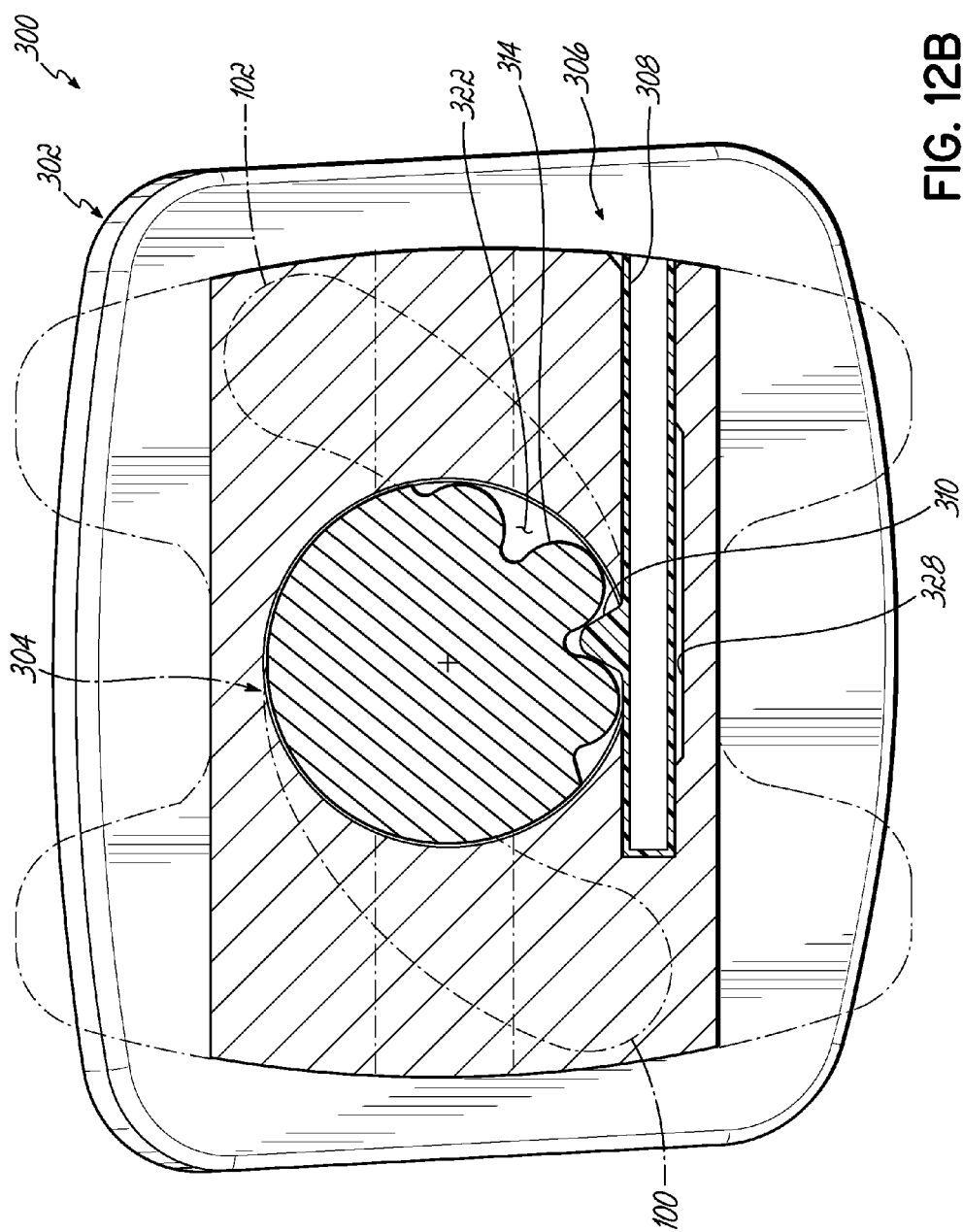
FIG. 12B is a cross-sectional view of the orthodontic bracket of FIG. 10 taken along section line 12-12 when the closure member is in a closed position.

With reference now to FIGS. 12A and 12B, when the rotating clip 304 is positioned within the cylindrical bore 58 of the bracket body 302, the wedge 310 projects into one trough 316. When so positioned, the clip 304 is prevented from being separated from the bracket body 302. In this regard, should the clip 304 be pulled away from the bracket body 302, such as in the labial direction, the lower bounding wall 322 of the groove 318 would contact the elongate tube 308, and, in particular, contact the wedge 310, and prevent movement of the clip 304 away from the bracket body 302. Accordingly, through the interaction of the elongate tube 308 and the groove 318, the clip 304 is secured to the bracket body 302. It should be noted, however, that the interaction between the elongate tube 308 and the bounding walls 320, 322 of the groove 318 does not restrict or otherwise prevent rotation of the clip 304 relative to the bracket body 302.

In addition to the above, the elongate tube 308 is configured to interact with the ratcheting mechanism 312, and, more particularly, the teeth 314, to provide a plurality of positive stops to the rotation of the clip 304 relative to the bracket body 302. In this regard, in a certain position of the clip 304 relative to the bracket body 302, one of the teeth 314 may confront the elongate tube 308, specifically the wedge 310, such that the wedge 308 meshes in one trough 316 between adjacent teeth 314. As shown in FIG. 12A, in this position, the retention arms 100, 102 are in the opened position.

Also, when in this position, the wedge 310 is positioned to directly interfere with rotation of the rotating clip 304 in either direction. More specifically, due to the arcuate surfaces of the teeth 314 and mating surfaces of the wedge 310, when the clip 304 is rotated as is indicated by arrows 326, the corresponding tooth 314 rides against the wedge 308 and thus resists rotation of the clip 304.

However, with a sufficiently high force or torque applied to the clip 304, the wedge 308 will deflect to flex or elastically deform the elongate tube 308. The wedge 310 is forced or pushed radially away from the rotating clip 304 so that the wedge 310 rides over the surface of the tooth 314. In this regard, the channel 70 may include a relief recess 328 generally opposite the wedge 310 to permit the elongate tube 308 to deflect into the relief recess 328 during maximum deflection of the wedge 310. When the tooth 314 passes by the wedge 310, the wedge 310 is extended into the adjacent trough 316 by the elastic bias of the elongate tube 308. In this position, the wedge 310 once again resists movement of the rotating clip 304 in either direction.

With reference to FIG. 12B, the wedge 310 is positioned between adjacent teeth 314 in the trough 316. However, the retention arms 100, 102 are in a closed position to retain an archwire in the archwire slot. While not shown, the orthodontic bracket 300 may include a position in which the rotating clip 304 is in an active closed position in which engagement elements (not shown in FIGS. 12A and 12B) extend from retention arms 100, 102 into the archwire slot and forcibly contact an archwire therein. This closed position may be between the position shown in FIG. 12A and the closed position shown in FIG. 12B.

Thus, a positive stop is provided in the rotation of the clip 304 when the wedge 310 is situated in a trough between adjacent teeth. The retention mechanism 306 may be designed such that the positive stops may correspond to one of the opened and/or closed positions, as shown. It will be appreciated that the bias on the elongate tube 308 when the wedge 310 is at its maximum deflection may be sufficient to cause spontaneous movement of the clip 304 as the clip 304 is moved slightly past the point of maximum deflection of the wedge 310 against the tooth 314. Once so positioned, the orientation of the mating surfaces of the wedge 310 against the tooth 314 may produce a torque on the rotating clip 304 sufficient to cause the rotating clip to spontaneously move to the nearest position. Furthermore, providing these positive stops may provide an orthodontist a tactile and/or audible click as the wedge 310 springs inward to relieve the elastic energy of the elongate tube 308. Of particular benefit is that the same retention mechanism provides both of these functions.

Figure 13A:
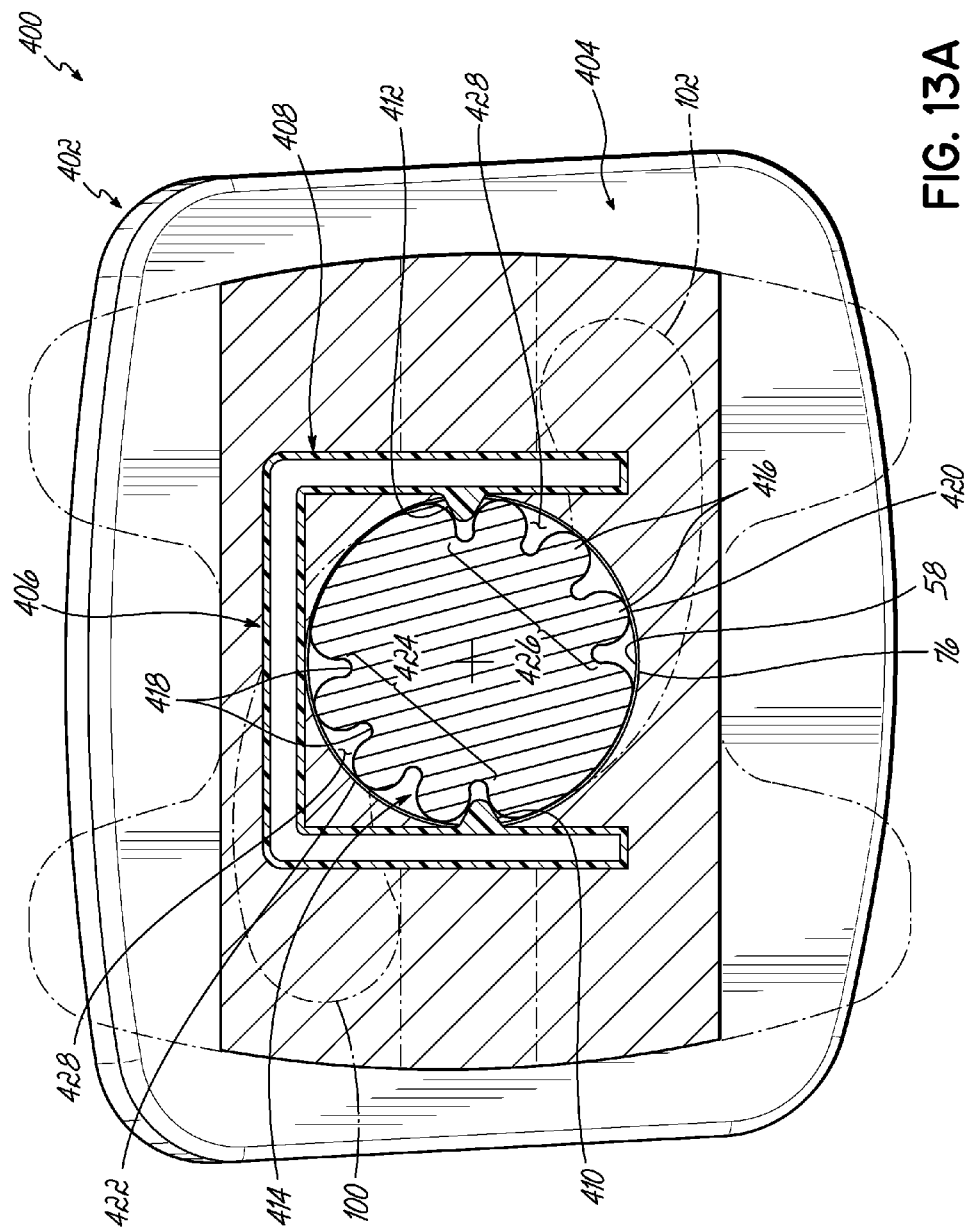
FIG. 13A is a cross-sectional view of one embodiment of a self-ligating orthodontic bracket, the closure member shown in the opened position.
Figure 13B:
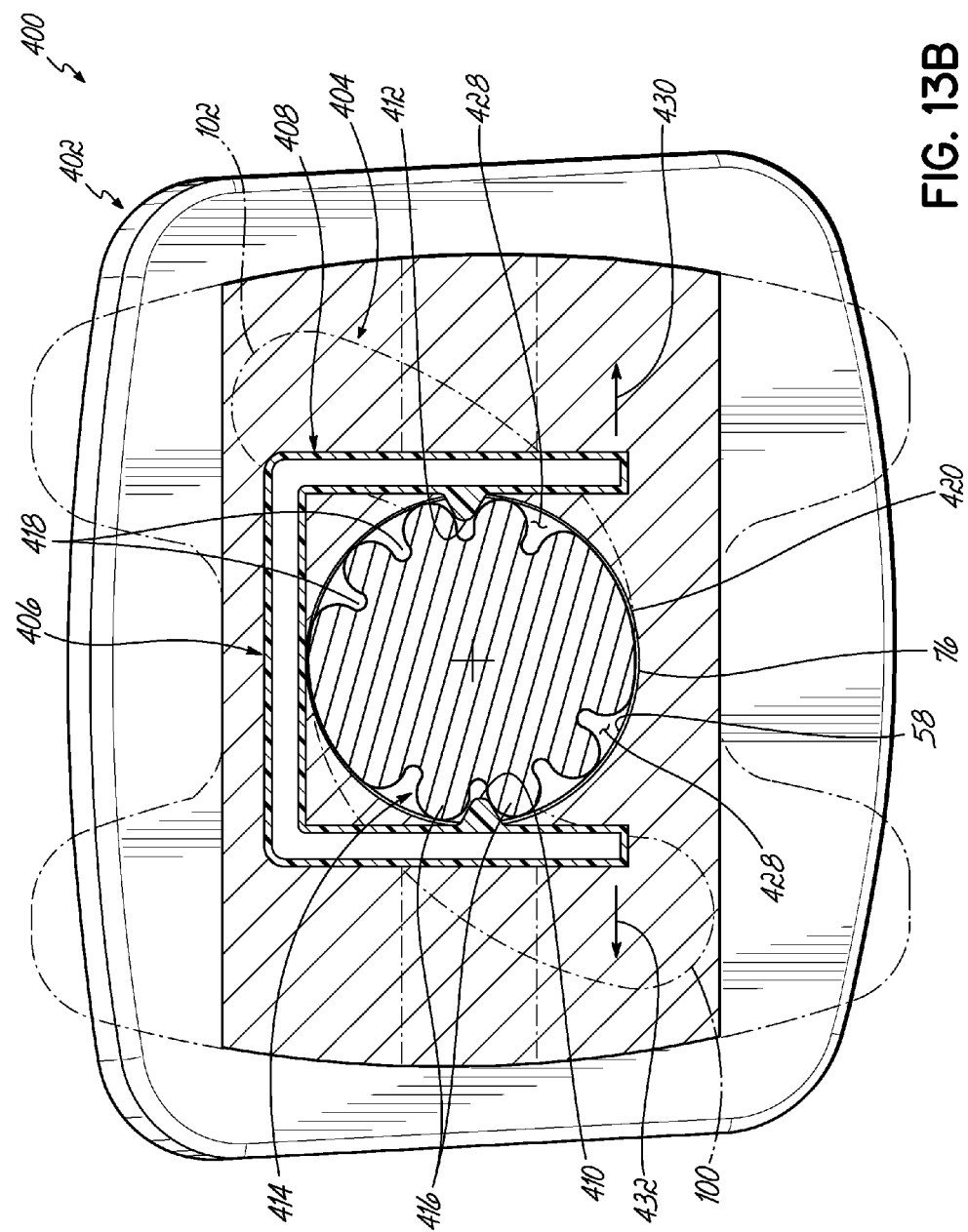
FIG. 13B is a cross-sectional view of the self-ligating orthodontic bracket of FIG. 13A, the closure member shown in the opened position.

In an alternative embodiment, and with reference to FIGS. 13A and 13B in which like reference numerals refer to like elements throughout the figures, an orthodontic bracket 400 includes a bracket body 402 similar to the bracket body 12 and the bracket body 302 and a rotating clip 404 similar to the rotating clip 14 and the rotating clip 304, described above, but differing in that a retention mechanism generally indicated at 406 has an alternative structural configuration than the retention mechanism 306 described above and shown in FIGS. 1-12B. While differing in structural configuration from the retention mechanism 130 and having similar structural features as the retention mechanism 306, the retention mechanism 406 has the same functions. That is, for example, to not only movably secure the clip 404 to the bracket body 402 such that the two elements cannot be separated, but also provide an indication of the rotational position of the clip 404 relative to the bracket body 402.

In regard to the former point, the retention mechanism 406 is configured to secure the clip 404 to the bracket body 402 such that, for example, the clip 404 cannot be pulled away from the bracket body 402 in the buccal or labial direction. While securing the clip 404 to the bracket body 402, the retention mechanism 406 is further configured to permit rotational movements of the clip 404 relative to the bracket body 402 between the opened position and one or more of the closed positions. In regard to the latter point, the retention mechanism 406 is configured to provide one or more positive stops in the rotation of the clip 404 relative to the bracket body 402.

In accordance with the embodiment described above, in one embodiment of the invention, and similar to the embodiments described above with reference to FIGS. 10-12B, the bracket body 402 includes a first aspect or element and the rotating clip 404 includes a second aspect or element, wherein the first and second elements are configured to interact with each other in a manner that movably (i.e., rotatably) secures the clip 404 to the bracket body 402 and provides at least one positive stop to the rotation of the clip 404 relative to the bracket body 402. In one embodiment, the first and second elements are configured to provide a plurality of positive stops to the rotation of the clip 404 relative to the bracket body 402.

In this regard, in one embodiment, the bracket body 402 includes a slot (not shown) extending generally in the occlusal-gingival direction from the gingival or occlusal sides. The slot intersects the cylindrical bore 58 at two locations, rather than at a single location as is the case with the channel 70. The retention mechanism 406 includes an elongate tube 408 having a generally U-shaped configuration and coupled to the bracket body 402 in the occlusal-gingival slot, for example, by laser welding the tube 408 to the bracket body 402. When inserted into the bracket body 402, the tube 408 intersects with the cylindrical bore 58 at opposing locations, for example, at the mesial and distal peripheral edges of the bore 58.

Figure 13C:
FIGS. 13C and 13D depict exemplary retention mechanisms.
Figure 13D:

In one embodiment, the elongate tube 408 is flexible or elastically deformable. For example, in one embodiment, the elongate tube 408 may be a hollow tube formed from NiTi, other superelastic materials, or other materials having some flexible or elastic properties. The shape of the elongate tube 408 includes a pair of bumps or wedges 410, 412 that generally extend away from the axis of the tube 408, and when inserted into the occlusal-gingival slot, project into the cylindrical bore 58. As an alternative to a tubular configuration shown, the retention mechanism 406 may include a solid wire configuration having bent portions in the configuration of wedges 410, 412. For example, the retention mechanism 406 may have a configuration similar to that of a dimpled archwire, (as is generally shown in FIGS. 13C and 13D) which is solid in cross section but has bends along its longitudinal axis. With regard to the elongate tube 408, the wedges 410, 412 interact with the rotating clip 404. In this regard, the first aspect of the retention mechanism 406 includes the elongate tube 408.

Further, and with reference to FIGS. 13A and 13B, the retention mechanism 406 includes a ratcheting mechanism 414 formed in or otherwise coupled to the rotating clip 404. The ratcheting mechanism 414 may be similar to the ratcheting mechanism 312 described above with respect to FIGS. 12A and 12B. As will be explained in further detail, the ratcheting mechanism 414 interacts with the elongate tube 408 to provide the functions described above, and thus the second aspect of the retention mechanism 406 includes the ratcheting mechanism 414. In one embodiment, the ratcheting mechanism 414 may be formed as part of the rotating clip 404. More particularly, the ratcheting mechanism 414 may be formed in the cylindrical base 76 of the clip 404.

In this regard, in one embodiment, the ratcheting mechanism 414 includes one or more teeth 416 separated by notches or troughs 418. The ratcheting mechanism 414 may be recessed into the side wall 86 of the cylindrical base 76 in grooves 420, 422 so as to divide the teeth 416 and corresponding troughs 418 into a first set 424 and second set 426 along the periphery of the rotating clip 404, as shown. Grooves 420, 422 may be defined by a pair of spaced-apart bounding side walls 428. The crests or lands of the teeth 416 may be coplanar with the surface of the cylindrical base 76, as shown. Alternatively, the teeth 416 may be recessed slightly below the surface of the cylindrical base 76. By way of example, and as illustrated, in one embodiment, each set 424, 426 may include three teeth 314 and three troughs 418. It should be realized that additional teeth and notches may be included, depending on the number of positive stops desired in the rotation of the clip 404. In addition, while the teeth are shown as having a generally arcuate configuration, embodiments of the present invention are not limited thereto, as other configurations may be utilized where it is desirable to modify the threshold force required to move the rotating clip 304 between any two positions, as is described above with reference to FIGS. 12A and 12B.

When the rotating clip 404 is positioned within the cylindrical bore 58 of the bracket body 402, wedges 410, 412 project into corresponding sets 424, 426 of teeth 416 and troughs 418. When so positioned, the clip 404 is prevented from being separated from the bracket body 402.

In this regard, should the clip 404 be pulled away from the bracket body 402, such as in the labial direction, the lower bounding wall 428 of one or both of grooves 420, 422 would contact the elongate tube 408, and, in particular, the corresponding wedges 410, 412 and prevent movement of the clip 404 away from the bracket body 402. Accordingly, through the interaction of the elongate tube 408 and the sets 424, 426 of teeth 416 and troughs 418, the clip 404 is secured to the bracket body 402. It should be noted, however, that the interaction between the elongate tube 408 and the bounding walls 428 of grooves 420, 422 does not restrict or otherwise prevent rotation of the clip 404 relative to the bracket body 402.

In addition to the above, the elongate tube 408 is configured to interact with the ratcheting mechanism 414, and more particularly, the teeth 416 to provide a plurality of positive stops to the rotation of the clip 404 relative to the bracket body 402. In this regard, in a certain position of the clip 404 relative to the bracket body 402, one of the teeth 416 in each set 424, 426 may confront the elongate tube 408, specifically the corresponding wedges 410, 412, such that each wedge 410, 412 meshes in one trough 418 of the corresponding set 424, 426. By way of example, as shown in FIG. 13A, in one position, the retention arms 100, 102 are in the opened position.

Also when in this position, each wedge 410, 412 is positioned to directly interfere with rotation of the rotating clip 404 in either direction. More specifically, due to the arcuate surfaces of the teeth 416 and mating surfaces of the each corresponding wedge 410, 412, when the clip 404 is rotated, the corresponding tooth 416 rides against a wedge 410, 412 and thus resists rotation of the clip 404. However, with a sufficiently high force or torque applied to the clip 404, the elongated tube 408 will deflect to flex or elastically deform. Each wedge 410, 412 is forced or pushed radially away from the rotating clip 304 so that the wedge 310 rides over the surface of the tooth 314. In this regard, while the elongated tube 408 may compress or deform along its cross section, the U-shaped configuration of the tube 408 may also flex mesially and/or distally, as is generally indicated by arrows 430, 432 in FIG. 13B, as torque is applied to the rotating clip 404. When each tooth 416 passes by the corresponding wedge 410, 412, the wedges 410, 412 spontaneously extend into troughs 418 by the elastic bias stored in the elongate tube 408. Once extended into troughs 418, the wedges 410, 412 resist movement of the rotating clip 404 in either direction. With reference to FIG. 13B, the wedges 410, 412 are positioned between teeth 416 in the trough 418 in respective grooves 420, 422. The retention arms 100, 102 are in a closed position to retain an archwire in the archwire slot.

Thus, a positive stop is provided in the rotation of the clip 404 when the wedges 410, 412 engage a corresponding trough 418. The retention mechanism 406 may be designed such that the positive stops may correspond to one of the opened and/or closed positions, as shown. It will be appreciated that the bias on the elongate tube 408 when the wedges 410, 412 are at their maximum deflection may be sufficient to cause spontaneous movement of the clip 404 as it is moved slightly past the point of maximum deflection of each wedge 410, 412. Once so positioned, the orientation of the mating surfaces of each wedge 410, 412 to a corresponding tooth 416 may produce a torque on the rotating clip 404 sufficient to cause the rotating clip to spontaneously move to the next position. Furthermore, providing these positive stops may provide an orthodontist a tactile and/or audible click as the wedges 410, 412 spring inward to relieve the elastic energy of the elongate tube 408 as the clip 404 moves to an opened and/or closed position. Of particular benefit is that the same retention mechanism provides both of these functions.

Figure 14A:
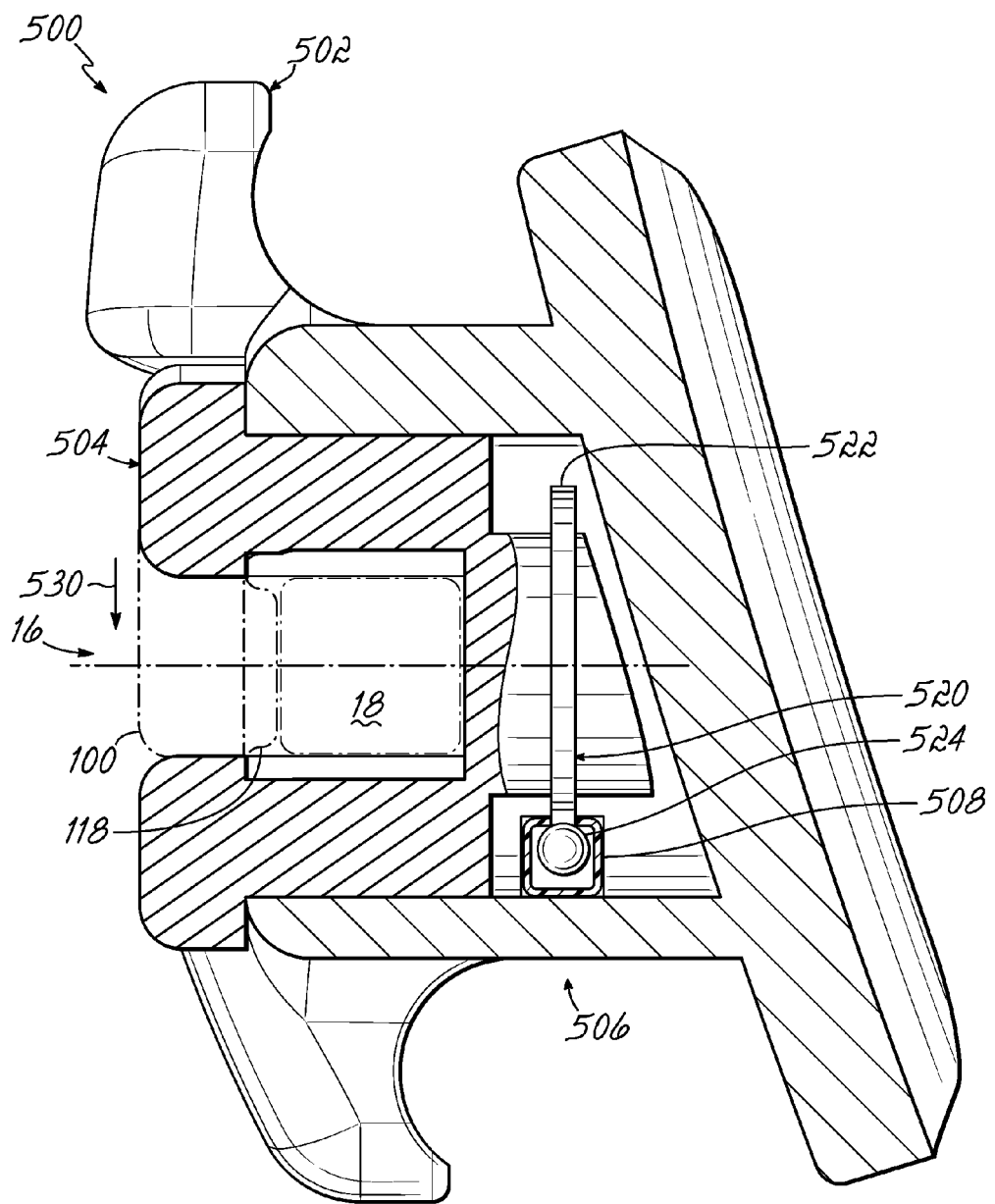
FIG. 14A is a cross-sectional view of one embodiment of a self-ligating orthodontic bracket of FIG. 10 taken along section line 14-14.
Figure 14B:
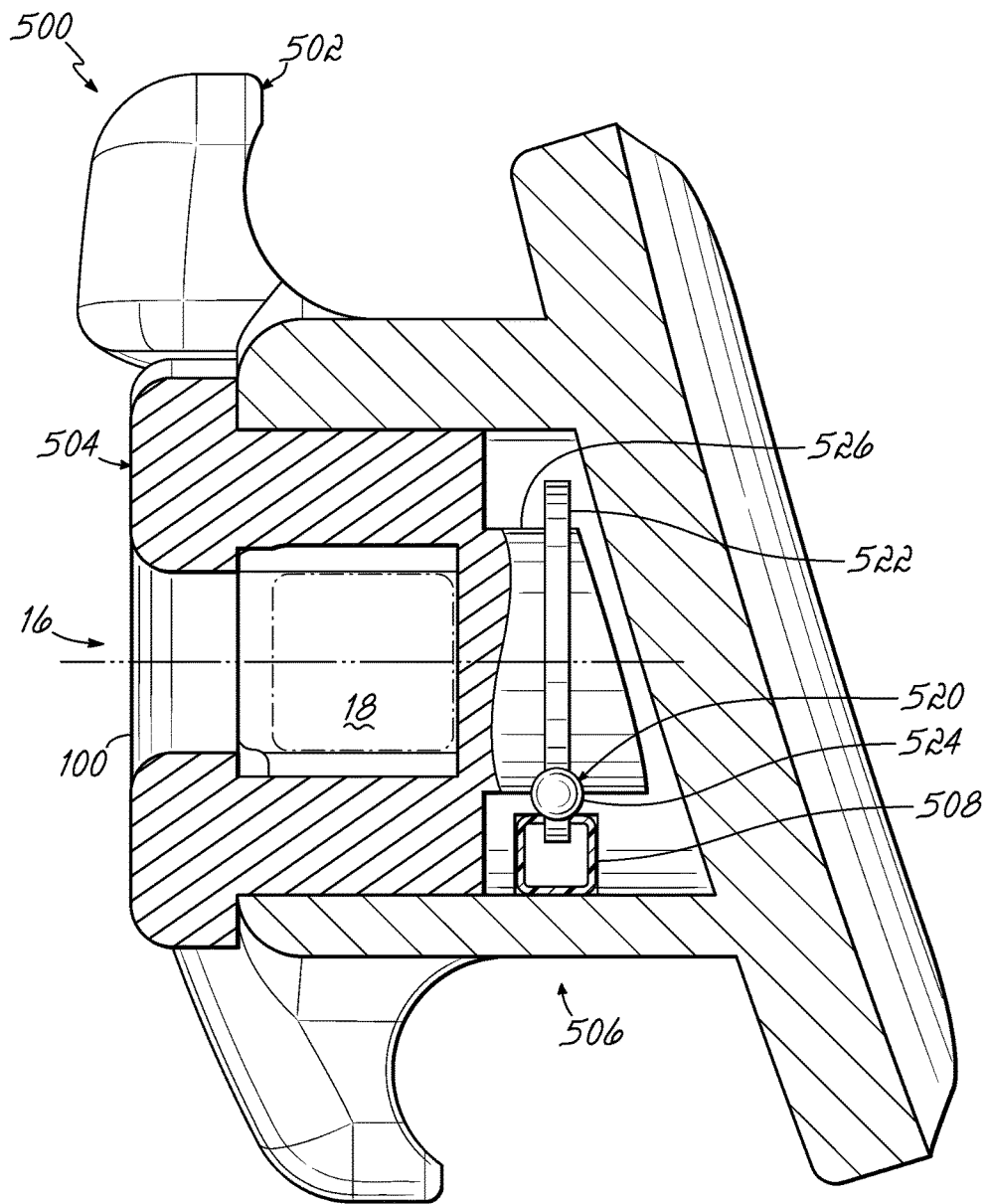
FIG. 14B is a cross-sectional view of the embodiment shown in FIG. 14A with the closure member in a different position.

In an alternative embodiment, and with reference to FIGS. 14A and 14B, in which like reference numerals refer to like elements throughout the figures, an orthodontic bracket 500 includes a bracket body 502, similar to the bracket bodies 12, 302, and 402, and a rotating clip 504, similar to the rotating clips 14, 304, and 404 described above, but differing in that a retention mechanism generally indicated at 506 has an alternative structural configuration than the retention mechanisms 130, 306, and 406 described above and shown in FIGS. 1-13B. While differing in structural configuration from the retention mechanisms described above, the retention mechanism 506 has the same functions. That is, for example, to not only movably secure the clip 504 to the bracket body 502 such that the two elements cannot be separated, but also provide an indication of the rotational position of the clip 504 relative to the bracket body 502.

In regard to the former point, the retention mechanism 506 is configured to secure the clip 504 to the bracket body 502 such that, for example, the clip 504 cannot be pulled away from the bracket body 502 in the buccal or labial direction. While securing the clip 504 to the bracket body 502, the retention mechanism 506 is further configured to permit rotational movements of the clip 504 relative to the bracket body 502 between the opened position and one or more of the closed positions. In regard to the latter point, the retention mechanism 506 is configured to provide one or more positive stops in the rotation of the clip 504 relative to the bracket body 502.

In accordance with the embodiment described above, in one embodiment of the invention, the bracket body 502 includes a first aspect or element and the rotating clip 504 includes a second aspect or element, wherein the first and second elements are configured to interact with each other in a manner that movably (i.e., rotatably) secures the clip 504 to the bracket body 502 and provides at least one positive stop to the rotation of the clip 504 relative to the bracket body 502. In one embodiment, the first and second elements are configured to provide a plurality of positive stops to the rotation of the clip 504 relative to the bracket body 502.

Figure 15A:
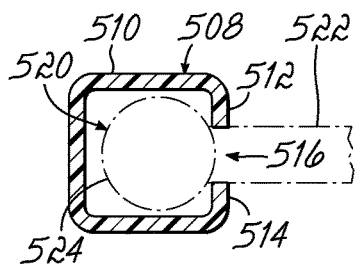
FIGS. 15A, 15B, and 15C are cross-sectional view of embodiment of a retention mechanism according to embodiments of the invention.
Figure 15B:
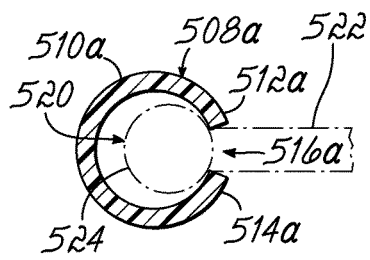
Figure 15C:
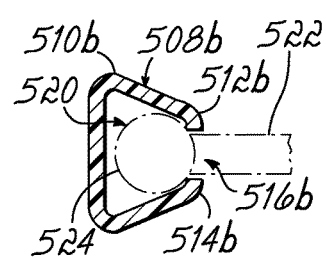

In this regard, in one embodiment, the bracket body 502 includes the channel 70 extending generally in the mesial-distal direction from one or both of the mesial or distal sides, as is described above in reference to FIGS. 1-9C. The retention mechanism 506 includes a split tube 508 and so differs in at least this respect from the elongated tubes described above. Generally, the split tube 508 may have a rectangular C-shaped configuration. It will be appreciated that the split tube 508 may have other cross-sectional configurations, such as a circular C-shaped configuration 508a and a wedge-shaped configuration 508b, as are depicted in FIGS. 15D and 15C. Unless specifically identified otherwise, it will be understood that each element in FIGS. 15B and 15C corresponds to a like-numbered element in FIGS. 14A, 14B, and 16A-16C but labeled with "a" or "b". Embodiments of the present invention are, however, not limited to the configurations shown in FIGS. 15A-15C, as other configurations having the functions described herein are within the scope of the present invention. When inserted into the bracket body 502, the tube 508 intersects with the cylindrical bore 58.

Figure 16A:
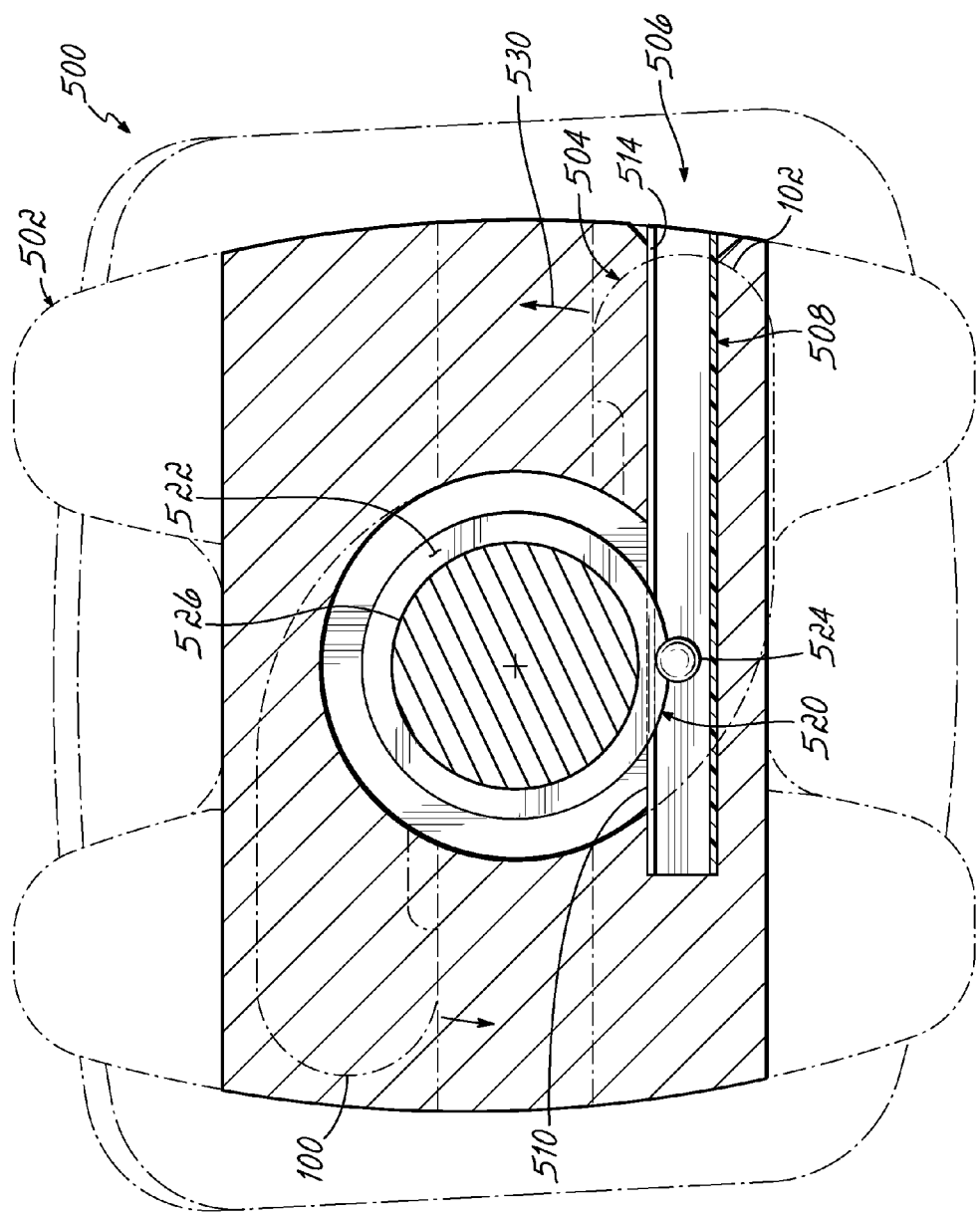
FIG. 16A is a cross-sectional view of the orthodontic bracket of FIG. 10 taken along section line 12-12 when the closure member is in the opened position.

In embodiments of the invention, and with reference to FIGS. 14A, 14B, and 16A, the split tube 508, is flexible or elastically deformable. For example, in one embodiment, the split tube 508 may be a hollow tube formed from NiTi, other superelastic materials, or other materials having some flexible or elastic properties. When inserted into the channel 70, a central portion 510 of the corresponding tube 508 extends into the cylindrical bore 58. The central portion 510 of the tube 508 interacts with the rotating clip 504, as described below. In particular, opposing side walls 512, 514 are separated by a slot 516 in the split tube 508. The side walls 512, 514 are flexible in a direction away from each other so as to permit widening of the slot 516. The first aspect of the retention mechanism 506 includes the elongate tube 508.

With reference to FIGS. 14A and 14B, the retention mechanism 506 includes a carriage mechanism 520 formed in or otherwise coupled to the rotating clip 504. The carriage mechanism 520 interacts with the split tube 508 to provide the functions described above, and thus the second aspect of the retention mechanism 506 includes the carriage mechanism 520. In one embodiment, the carriage mechanism 520 may be formed as part of the rotating clip 504. More particularly, the carriage mechanism 520 may be formed in the cylindrical base 76 of the clip 504.

In this regard, in one embodiment, the carriage mechanism 520 includes a lip or runner 522 along which there is a projection, such as, a ball-like member 524. The ball-like member 524 may be an enlarged projection extending from the runner 522 in at least a labial-lingual direction and may also extend radially beyond the circumferential surface of the runner 522. While the ball-like member 524 is shown as having a generally spherical shape, embodiments of the invention are not limited to having this configuration, as other shaped projections are within the scope of the present invention. The carriage mechanism 520 may be recessed into the side wall 86 of the cylindrical base 76 around its entire circumference, as shown, so that the runner 522 and ball-like member 524 project from a hub 526 and so are positioned to interact with the portion 510 of the tube 508. It will be appreciated that the carriage mechanism 520 need not extend the entire circumference of the rotating clip 504 and so the mechanism 520 may be formed in a recess within the cylindrical base 76. While the ball-like mechanism 524 is shown as having a generally spherical configuration extending from the runner 522, embodiments of the present invention are not limited thereto, as other configurations may be utilized where it is desirable to modify the threshold force required to move the rotating clip 504 between any two positions, as is described below.

When the rotating clip 504 is positioned within the cylindrical bore 58 of the bracket body 502, the portion 510 of the tube 508 interacts with the carriage mechanism 520. In particular, the tube 508 interacts with at least the runner 522 as the clip 504 is rotated. As shown in FIGS. 14A, 14B, and 15A-15C, the runner 522 extends through the slot 516 of the tube 508 in each rotational position of the clip 504 and so prevents the clip 504 from being separated from the bracket body 502. In this regard, should the clip 504 be pulled away from the bracket body 502, such as in the labial direction, the runner 522 would contact the side wall 512 and prevent movement of the clip 504 away from the bracket body 502. Accordingly, through the interaction of the split tube 508 and the carriage mechanism 520, the clip 504 is secured to the bracket body 502. It should be noted, however, that the interaction between the tube 508 and the runner 522 does not restrict or otherwise prevent rotation of the clip 504 relative to the bracket body 502.

In addition to the above, and with reference to FIGS. 14A, 14B and 16A-16C, the split tube 508 is configured to interact with the carriage mechanism 520, and more particularly, the ball-like mechanism 524 to provide at least one positive stop to the rotation of the clip 504 relative to the bracket body 502. In this regard, in at least one position of the clip 504 relative to the bracket body 502, the ball-like member 524 may confront the split tube 508 such that the rotating clip 504 is prevented from inadvertent rotation in at least one direction. By way of example, as shown in FIGS. 14A and 16A, the ball-like member 524 resides within the interior of the split tube 508 with the runner 522 extending between the sidewalls 512, 514. By way of example only, when the ball-like mechanism is so situated, the retention arms 100, 102 may be in the opened position (as is shown in phantom line in FIG. 16A). Rotation of the rotating clip 504 from this position in either direction causes the ball-like member 522 to contact at least the sidewalls 512, 514 and prevent inadvertent rotation of the clip 504.

Figure 16B:
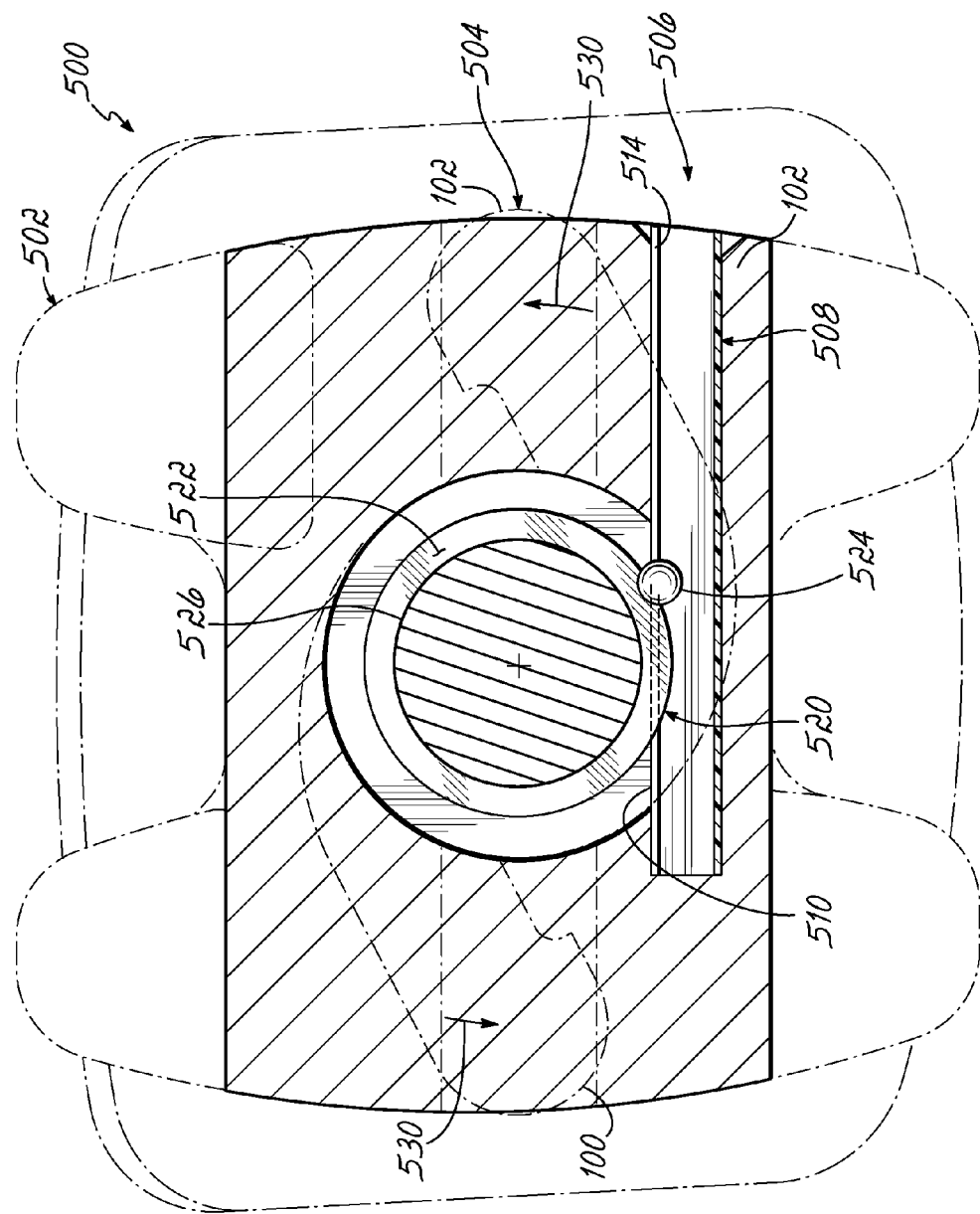
FIG. 16B is a cross-sectional view of the orthodontic bracket of FIG. 10 taken along section line 12-12 when the closure member is in a closed position.

With a sufficiently high force or torque applied to the clip 504, as is generally indicated by arrows 530 in FIGS. 16A and 16B, the split tube 508 will flex or elastically deform. In this regard, the ball-like member 524, because it is larger in the labial-lingual dimension than the slot 516, will wedge the sidewalls 512, 514 away from one another to elastically deform the central portion 510 of the tube 508 and, specifically, to enlarge the slot 516. The ball-like member 524 may then push through the enlarged slot 516 upon continued rotation of the clip 504. Although not shown, the sidewall 512 may deflect in a labial direction while the sidewall 514 may deflect in a lingual direction to enlarge the slot 516 as the ball-like member 524 forces its way through the slot 516. In this way, at least the central portion 510 of the split tube 508 elastically deforms, as torque is applied to the rotating clip 504.

In one embodiment, an archwire may be actively ligated when the ball-like member 524 is pinched between the sidewalls 512, 514, as is shown in FIG. 16B. That is, when the torque on the clip 504 is sufficient to wedge the ball-like member 524 in the slot 516, the retention members 100, 102 may be in a closed position so that the engagement element 118 contacts the archwire 18 in the slot 16 (shown in phantom line in FIG. 14A). In this orientation, the pinching action of the central portion 510 of the tube 508 on the ball-like member 524 alone or in addition to any active ligation forces from the archwire 18 on the clip 504 may resist inadvertent movement of the rotating clip 504 in either direction.

Figure 16C:
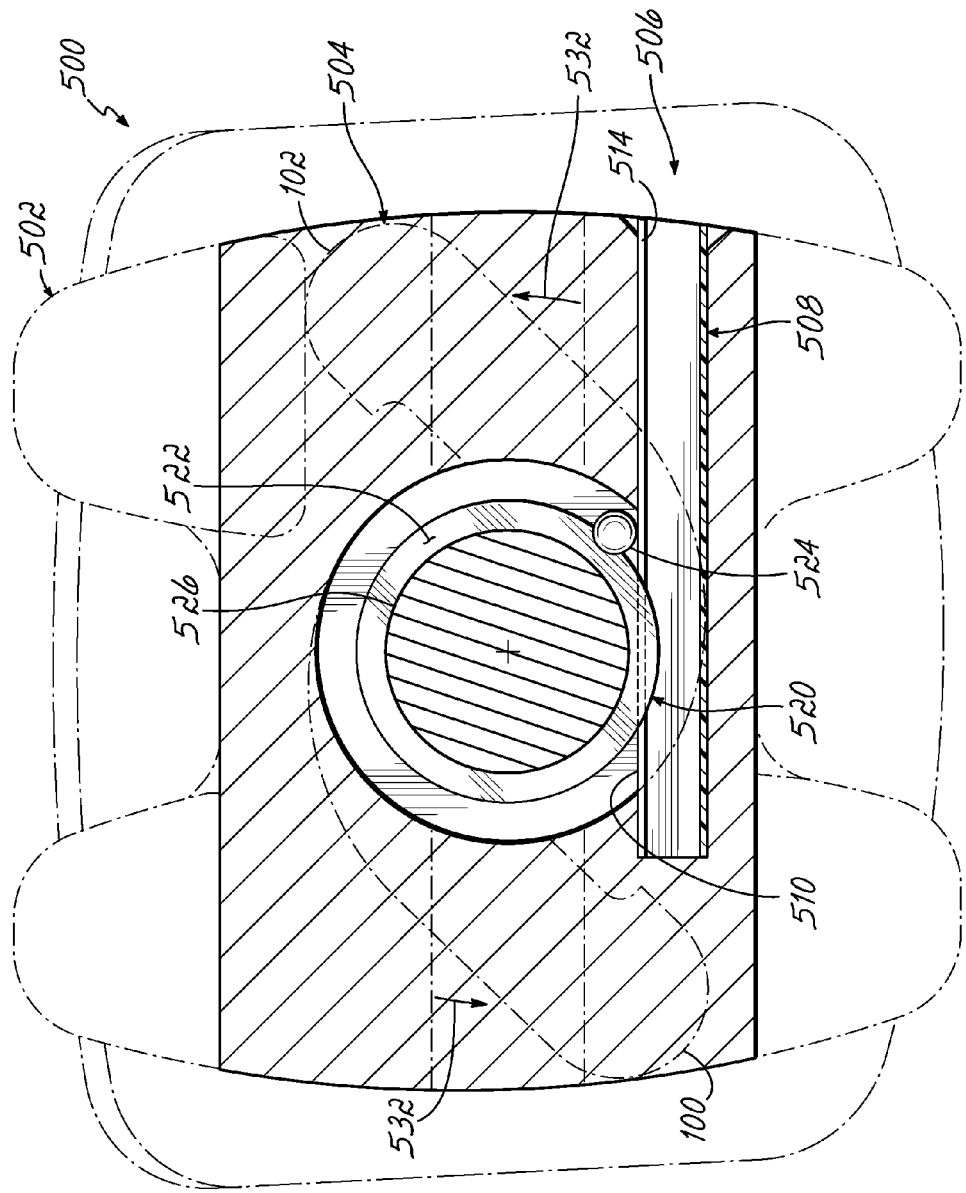
FIG. 16C is a cross-sectional view of the orthodontic bracket of FIG. 10 taken along section line 12-12 when the closure member is in another closed position.

With reference now to FIGS. 14B and 16C, further rotation of the clip 504 in a counterclockwise direction, as is generally indicated by arrows 532, rotates the ball-like member 524 from between the sidewalls 512, 514. This may be accomplished with significantly less torque than that required to deflect the sidewalls 512, 514 with the ball-like member 524. In this way, the rotating clip 504 may be rotated to another closed position in which the retention arms 100, 102 passively ligate the archwire 18 in the archwire slot 16, as is shown in FIG. 14B. It will be appreciated that the pinching force on the ball-like member 524 when the sidewalls 510, 512 are at their maximum deflection may be sufficient to cause spontaneous movement of the clip 504 as it is moved slightly past the point of maximum deflection of each sidewall 512, 514. Slightly past the point of maximum deflection of the sidewalls 512, 514, the orientation of the mating surfaces of each sidewall 510, 512 on the surface of the ball-like member 524 may produce a torque on the rotating clip 504 sufficient to cause it to spontaneously move to the next nearest position. Furthermore, the configuration of the ball-like mechanism 524 and the split tube 508 may provide an orthodontist a tactile and/or audible click as the sidewalls 510, 512 spring inward to relieve the elastic energy of the split tube 508 as the clip 504 rotates to an opened and/or closed position.

Once in the position shown in FIGS. 14B and 16C, the ball-like member 524 is proximate the central portion 510, but is external of the tube 508 though the runner 522 extends into the slot 516. Rotation of the clip 504 in the direction opposite the arrows 532 in FIG. 16C causes the ball-like member 524 to abut the sidewalls 512, 514. Thus, in this orientation a positive stop is provided in the rotation of the clip 504 when the ball-like member 524 engages exterior of the tube 508. The retention mechanism 506 may be designed such that the positive stops may correspond to one of the opened and/or closed positions, as shown. It will be appreciated that in an alternative embodiment (not shown), the ball-like member 524 may provide a positive stop for each of the opened and the two closed positions. In other words, unlike the embodiment shown in FIGS. 14A-16C, the ball-like member 524 may abut the tube 508 in the opened position, abut the tube 508 in an active ligation position (which is unlike that shown in FIG. 16B), and abut the tube 508 in a passive ligation position. Of particular benefit is that the same retention mechanism provides both of these functions.

As described above, it will be appreciated that embodiments of the invention are not limited to the direction of rotation of the ligating member. In this regard, the ligating member may be rotated from the opened position to each of the closed positions by a continuous clockwise or continuous counterclockwise movement. More specifically, the ligating member may be rotated from the opened position to a first closed position by a first clockwise (or counterclockwise) rotation. A second clockwise (or counterclockwise) rotation may position the ligating member at a second closed position.

In an alternative embodiment, the ligating member may be rotated from an opened position to a first closed position by a rotation in first direction (e.g., clockwise). The ligating member may be rotated from the opened position to a second closed position by rotation in a second direction (e.g., counterclockwise) opposite to that of the first direction. For example, to move the ligating member from a first closed position to a second closed position, the ligating member may be rotated counter clockwise to the opened position and again counterclockwise to the second closed position. Though not described, embodiments of the present invention may include rotations in the reverse direction from that described above.

With reference to FIGS. 17A-17C and 18A-18C, embodiments of the invention may include an orthodontic bracket 600 having a bracket body 602 and a rotating clip 604. While similar to the orthodontic brackets described above, the rotating clip 604 may include four retention arms 606, 608, 610, and 612. The bracket 600 may further include a retention mechanism 614, similar to the retention mechanism 506, described above, to not only movably secure the clip 604 to the bracket body 602 such that the two elements cannot be separated, but also provide an indication of the rotational position of the clip 604 relative to the bracket body 602.

In this regard, in one embodiment, the bracket body 602 includes the channels (not shown) extending generally in the mesial-distal direction from one or both of the mesial or distal sides, as is described above in reference to FIGS. 1-9C. The retention mechanism 614 includes a pair of split tubes 616, 618 (shown in FIGS. 18A-18C) similar to the split tube 508.

Figure 18C:
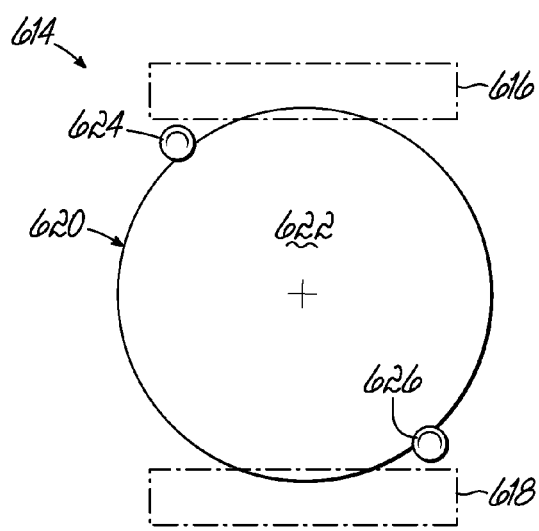
FIGS. 18A, 18B, and 18C are plan views of one embodiment of a retention mechanism showing different orientations of the retention mechanism corresponding to the orientations of the ligating member shown in FIGS. 17A, 17B, and 17C, respectively.
Figure 18A:
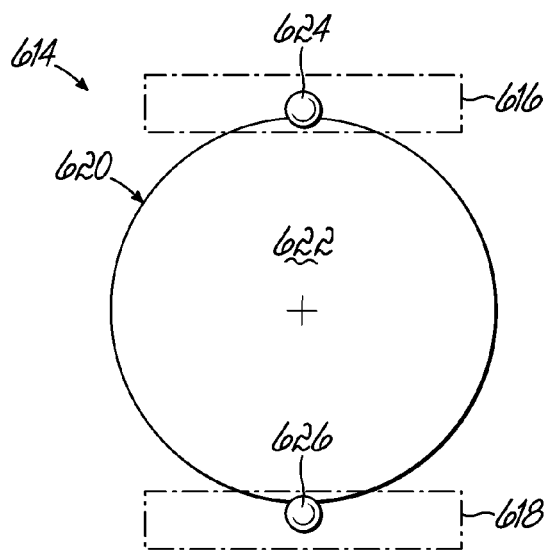
Figure 18B:
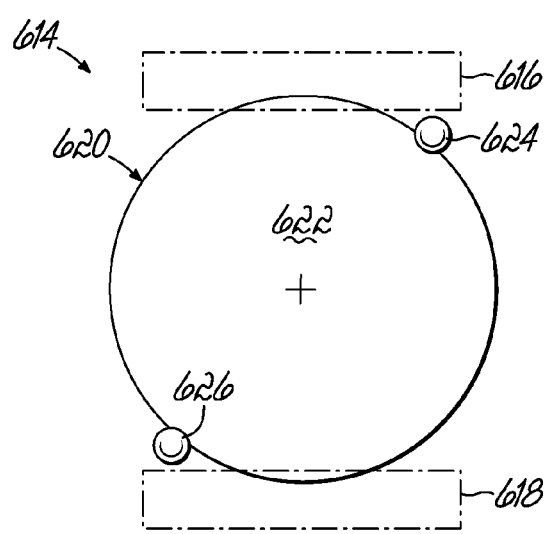

With reference to FIGS. 18A-18C, the retention mechanism 614 includes a carriage mechanism 620 formed in or otherwise coupled to the rotating clip 604. The carriage mechanism 620 interacts with the split tubes 616, 618 to retain the clip 604 in the bracket body 602 and includes a runner 622 and a pair of projections, such as, a pair of ball-like member 624, 626, similar to that described above.

Figure 17C:
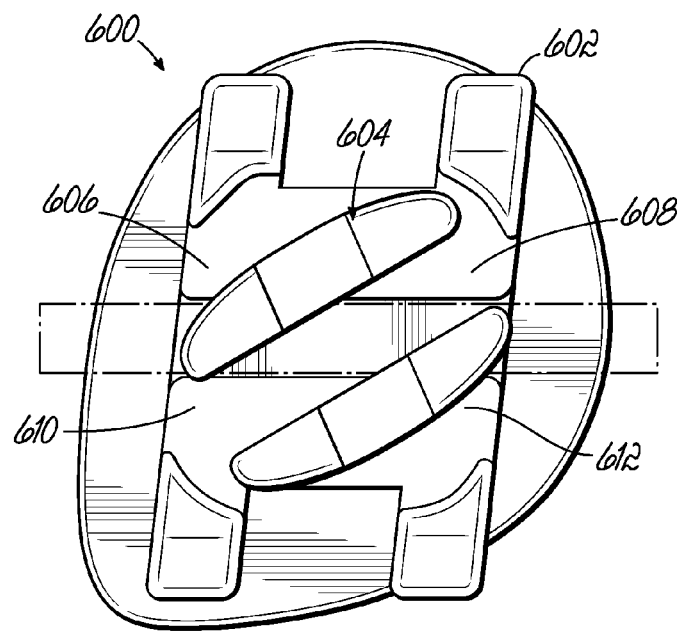
FIGS. 17A, 17B, and 17C are plan views of one embodiment of the invention with the ligating member shown in different orientations.
Figure 17A:
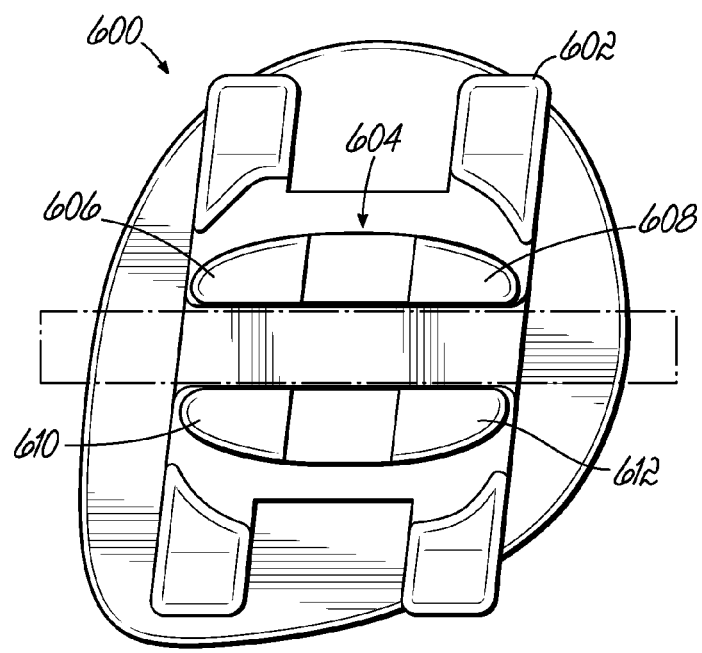
Figure 17B:
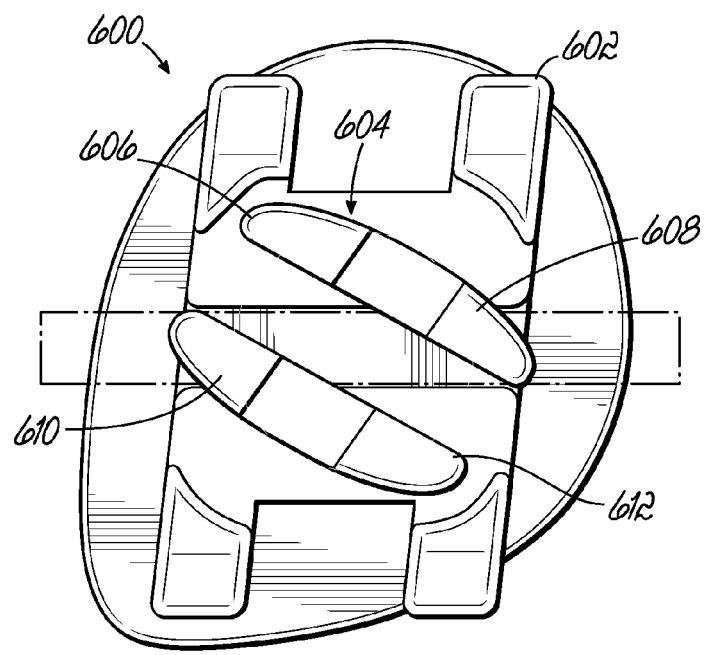

Once in the opened position shown in FIGS. 17A and 18A, the ball-like members 624, 626 are internal to the corresponding split tubes 616, 618, and so the rotation clip 604 is retained in the opened position. Rotation of the clip 604 in one direction (e.g. clockwise) as shown in FIGS. 17B and 18B causes the ball-like member 624, 626 to abut the sidewalls of the split tubes 616, 618. Thus, in this orientation, a positive stop is provided in the rotation of the clip 604 when the ball-like members 624, 626 engage the interior of the corresponding tubes 616, 618. The retention mechanism 614 may be designed such that the positive stops may correspond to the opened position, as shown.

Rotation of the clip 604 in either the clockwise direction or the counterclockwise direction with sufficient torque rotates a pair of the retention arms 606, 608, 610, and 612 over the archwire slot 18. For example, rotation of the clip 604 in the clockwise direction forces the ball-like members 624, 626 from within the split tubes 616, 618, as shown, and rotates the retention arms 606 and 608 over the archwire 18. In this orientation, the retention arms 606 and 608 retain the archwire 18 in the archwire slot 16 and may either activity ligate or passively ligate the archwire 18. Rotation of the rotating member 604 in the counterclockwise direction from the position shown in FIG. 17A, for example, as shown in FIG. 17C, may rotate the other retention arms 610 and 612 over the archwire slot 18 to retain the archwire 16 in the slot 18. Again, the retention arms 610 and 612 may either actively or passively ligate the archwire 18 in the slot 16.

Specifically, in one embodiment, the retention arms 610 and 612 actively ligate the archwire 16 and the retention arms 606 and 608 passively ligate the archwire 16. Thus, by moving the rotating clip 604 in one rotational direction, passive ligation may be achieved and by rotating the clip 604 in the opposite direction active ligation may be achieved with retention arms 610 and 612. In either or both of the closed positions, whether active or passive, the ball-like members 624, 626 may abut a corresponding split tube 616, 618 (as shown in FIGS. 18B and 18C) so as to form a positive stop to resist inadvertent rotation of the clip 604 to the opened position (as shown in FIGS. 17A and 18A), similar to that described in the preceding paragraphs.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in any combinations depending on the needs and preferences of the user.

What is claimed is:

1. An orthodontic bracket for coupling an archwire with a tooth, comprising:
   a bracket body configured to be mounted to the tooth, the bracket body including an archwire slot adapted to receive the archwire therein and a channel;
   a rotatable closure member movable relative the bracket body between an opened position and at least one closed position about an axis of rotation that intersects the archwire slot; and a retention mechanism having a first element associated with the bracket body and a second element associated with the closure member, the first and second elements cooperating to rotatably secure the closure member to the bracket body and to provide at least one positive stop in the rotation of the closure member relative to the bracket body, wherein the first element includes a first flexible elongate member secured to the bracket body in the channel such that at least a portion of the first flexible elongate member is fixed against movement relative to the bracket body.

2. The orthodontic bracket of claim 1, wherein the closure member is rotatable between an opened position and at least two closed positions.

3. The orthodontic bracket of claim 2, wherein one closed position provides active ligation of the archwire in the archwire slot and another closed position provides passive ligation of the archwire in the archwire slot.

4. The orthodontic bracket of claim 2, wherein the closure member rotates in a first direction to move the closure member from the opened position to a first closed position and is further rotated in the first direction to move the closure member from the first closed position to a second closed position.

5. The orthodontic bracket of claim 2, wherein the closure member rotates in a first direction to move the closure member from the opened position to a first closed position and is rotated in a second direction to move the closure member from the opened position to a second closed position.

6. The orthodontic bracket of claim 1, wherein the archwire slot includes opposed slot surfaces extending from a base surface and the rotating closure member includes at least two retaining arms that oppose the base surface of the archwire slot in the at least one closed position for retaining the archwire in the archwire slot.

7. The orthodontic bracket of claim 6, wherein the rotating closure member includes four retaining arms for retaining the archwire in the archwire slot.

8. The orthodontic bracket of claim 1, wherein the first and second elements of the retention mechanism cooperate to provide a plurality of positive stops in the rotation of the closure member.

9. The orthodontic bracket of claim 8, wherein the opened position and the at least one closed position correspond to a positive stop in the rotation of the closure member.

10. The orthodontic bracket of claim 1, wherein the second element comprises a cam mechanism on the closure member.

11. The orthodontic bracket of claim 10, wherein the first flexible elongate member comprises an elongate tube.

12. The orthodontic bracket of claim 10, wherein the cam mechanism comprises a groove in the closure member having a base wall and a pair of side walls extending away from the base wall, wherein at least a portion of the first flexible elongate member is positioned in the groove.

13. The orthodontic bracket of claim 12, wherein the first flexible elongate member interacts with a side wall of the groove to prevent the closure member from being separated from the bracket body.

14. The orthodontic bracket of claim 12, wherein the base wall of the groove interacts with the first flexible elongate member to provide the at least one positive stop in the rotation of the closure member.

15. The orthodontic bracket of claim 14, wherein the base wall of the groove includes a plurality of flats with adjacent flats separated by an apex, wherein a positive stop is defined when a flat of the groove confronts the first flexible elongate member, and the apex between adjacent flats provides resistance to rotation of the closure member away from the positive stop.

16. The orthodontic bracket of claim 14, wherein the base wall of the groove includes a plurality of flats with adjacent flats separated by an apex, wherein a positive stop is defined when the apex engages with a cutout or indentation in the first flexible elongate member.

17. The orthodontic bracket of claim 1, wherein the first flexible elongate member is on a first side of the archwire slot and a second flexible elongate member is on a second side of the archwire slot, wherein the second element comprises a cam mechanism comprising a groove on a first side of the closure member and a cam surface on a second side of the closure member, wherein the first flexible elongate member interacts with the groove to prevent the closure member from being separated from the bracket body, and wherein the second flexible elongate member interacts with the cam surface to provide at least one positive stop in the rotation of the closure member.

18. The orthodontic bracket of claim 17, wherein the first flexible elongate member interacts with the groove to provide a positive stop in the rotation of the closure member.

19. The orthodontic bracket of claim 1, wherein the second element comprises a ratcheting mechanism on the closure member.

20. The orthodontic bracket of claim 19, wherein the ratcheting mechanism is within a groove having at least one side wall and the first flexible elongate member interacts with the side wall to prevent the closure member from being separated from the bracket body.

21. The orthodontic bracket of claim 19, wherein the first flexible elongate member includes a projection and the ratcheting mechanism includes one or more teeth and one or more troughs, and wherein the projection interacts with the teeth to provide the at least one positive stop in the rotation of the closure member.

22. The orthodontic bracket of claim 21, wherein the at least one positive stop corresponds to when the projection is positioned in one of the troughs.

23. The orthodontic bracket of claim 21, wherein the number of positive stops corresponds to the number of troughs.

24. The orthodontic bracket of claim 19, wherein the first flexible elongate member is generally U-shaped and includes a pair of opposing projections and the ratcheting mechanism includes one or more teeth and one or more troughs and each projection of the pair of projections interacts with teeth to provide the at least one positive stop in the rotation of the closure member.

25. The orthodontic bracket of claim 1, wherein the second element comprises a carriage mechanism on the closure member.

26. The orthodontic bracket of claim 25, wherein the first flexible elongate member has a slot and the carriage mechanism includes a runner and a ball-like member extending from the runner, and wherein the runner extends into the slot to prevent the closure member from being separated from the bracket body.

27. The orthodontic bracket of claim 26, wherein the ball-like member is sized to form an interference fit with the slot so as to provide the at least one positive stop in the rotation of the closure member.

28. An orthodontic bracket for coupling an archwire with a tooth, comprising:

a bracket body that is configured to be mounted to the tooth and includes an archwire slot and a channel;

a rotatable closure member that is movable relative the bracket body between an opened position and at least one closed position about an axis of rotation that intersects the archwire slot, and includes a groove; and a retention mechanism that includes a flexible elongate member secured to the bracket body in the channel such that at least a portion of the flexible elongate member is fixed relative to the bracket body, and extending into the groove so as to rotatably secure the rotatable closure member to the bracket body and to provide at least one positive stop in the rotation of the closure member.

29. The orthodontic bracket of claim 28, wherein the bracket body includes at least one of a mesial side, a distal side, an occlusal side, and a gingival side, and wherein the channel is open to at least one of the mesial side, the distal side, the occlusal side, and the gingival side.

30. The orthodontic bracket of claim 28, wherein the groove includes a base wall and a pair of side walls extending away from the base wall.

31. The orthodontic bracket of claim 30, wherein the groove defines a cam mechanism.

32. The orthodontic bracket of claim 28, wherein the channel extends substantially parallel to the archwire slot.

* * * * *